United States Patent [19]

Jezl et al.

[11] Patent Number: 4,751,336
[45] Date of Patent: Jun. 14, 1988

[54] CONVERSION OF A LOWER ALKANE

[75] Inventors: James L. Jezl, St. Charles; Glenn O. Michaels, South Holland; Michael J. Spangler, Dolton, all of Ill.

[73] Assignee: Amoco Corporation, Chicago, Ill.

[21] Appl. No.: 706,732

[22] Filed: Feb. 28, 1985

[51] Int. Cl.$^4$ .............................................. C07C 2/00
[52] U.S. Cl. ................................... 585/324; 585/322; 585/500; 585/541; 585/654; 585/656; 585/658; 585/661; 585/700; 585/943
[58] Field of Search ............... 585/324, 322, 500, 541, 585/654, 656, 658, 661, 700, 943

[56] References Cited

U.S. PATENT DOCUMENTS

| | | | |
|---|---|---|---|
| 3,845,156 | 10/1974 | Farha | 585/656 |
| 4,523,049 | 6/1985 | Jones et al. | 585/500 |
| 4,523,050 | 6/1985 | Jones et al. | 585/500 |
| 4,544,787 | 10/1985 | Breder, Jr. | 585/500 |

FOREIGN PATENT DOCUMENTS 150886  9/1981  Fed. Rep. of Germany ...... 585/822

OTHER PUBLICATIONS

8th Int. Congress in Catalysts, Hinsen, Bytyn and Baerns, Oxidative Dehydrogenation and Coupling of Methane, pp. 581–593 (Jul., 1984).
Fang et al., Catalytic Pyrolysis of Methane, J. Chinese Chem. Soc., 29, 265–273.
Hinsen and Baerns, Chemical Zeitung, 107, 223–226 (1983).
Keller and Bhasen, Synthesis of Ethylene via Oxidative Coupling of Methane, J. of Catalysis, 73, 9–19(1982).

Primary Examiner—William R. Dixon, Jr.
Assistant Examiner—Jerry D. Johnson
Attorney, Agent, or Firm—John B. Goodman; William H. Magidson; Ralph C. Medhurst

[57] ABSTRACT

The catalyzed oxidative coupling of a lower molecular weight alkane to higher molecular weight hydrocarbons which are then oxidatively dehydrogenated to form unsaturated aliphatic hydrocarbons is disclosed.

27 Claims, 1 Drawing Sheet

CONVERSION OF A LOWER ALKANE

BACKGROUND OF THE INVENTION

1. Field of the Invention

This invention relates generally to the conversion of a lower molecular weight alkane to more valuable, higher molecular weight hydrocarbons, and more particularly concerns an aforesaid process which comprises the oxidative coupling of the alkane.

2. Description of the Prior Art

A major source of lower molecular weight alkanes is natural gas. Lower molecular weight alkanes are also present in coal deposits and are formed during numerous mining operations, in various petroleum processes and in the above- or below-ground gasification or liquefaction of coal, tar sands, oil shale and biomass.

It is highly desirable to convert lower molecular weight alkanes to more valuable, higher molecular weight materials and a number of attempts to do so have been reported. For example, G. E. keller and M. M. Bhasin (J. Catal. 73, 1982, 9-19) have shown that in the presence of catalysts methane can be converted to $C_2$ hydrocarbons, but that the yields of ethylene and ethane are low and amount to only from 10 to 50 percent of the reacted methane. To improve the selectivity for the production of the desired $C_2$ hydrocarbons and to suppress the undesirable further reaction of the $C_2$ hydrocarbons initially formed to produce carbon dioxides, Keller and Bhasin propose a special reaction method: the catalyst is first charged with oxygen by the passage over it of a gas containing oxygen; then in a second step, the oxygen in the gas chamber of the catalytic reactor is replaced by an inert gas; in a third step, methane is fed over the catalyst which partially produces the desired reaction; in a fourth and last step, an inert gas is again led through the reactor to supplant the residual methane and the resulting product, before the sequence of steps is repeated. In this process, depending on the catalyst used and the temperature selected, the selectivities for the production of $C_2$ hydrocarbons range from about 5 to about 45%, and the selectivities for the production of $CO_2$ range from about 55 to 95%, with the conversions of methane ranging between 1 and 10%.

Keller and Bhasin arrive at the conclusion that the oxidative coupling is only highly selective to the higher hydrocarbons when the reaction takes place in the absence of gas-phase oxygen and the oxidative coupling of the hydrocarbons should be caused by reaction with the lattice oxygen of the metal oxides, which are thus reduced by two valency stages. Since the lattice oxygen available in the catalyst is predetermined, for every measured unit of the catalyst only a limited quantity of hydrocarbons can be reacted.

It is evident that the modus operandi in Keller and Bhasin is costly in terms of apparatus as well as being simultaneously linked with small yields in space-time terms and high operating and investment costs. Moreover, the attainable methane conversions and/or the resultant space-time yields are too small for a commercial installation according to the data of the authors. Furthermore, the only products reported are $C_2$ hydrocarbons.

Jones et al., U.S. Pat. Nos. 4,443,664-9 disclose methods for synthesizing hydrocarbons containing as many as 7 carbon atoms from a methane source which comprise contacting methane with a reducible oxide of antimony, germanium, bismuth, lead, indium or manganese. These patents also disclose that the reducible oxides can be supported by a conventional support material such as silica, alumina, titania, and zirconia. Specific supports disclosed are Houdry HSC 534 silica, Cab-O-Sil, Norton alpha-alumina and Davison gamma-alumina. The ranges of reaction temperatures disclosed in the aforesaid patents are from a lower limit of 500° C. to an upper limit of 800° C.–1000° C. In the disclosed processes, the reducible oxide is first reduced and is then regenerated by oxidizing the reduced composition with molecular oxygen, either in a second zone or by alternating the flow of a first gas comprising methane and the flow of an oxygen-containing gas. The highest yield of hydrocarbon products reported was only about 2.1% of the methane feed, when a reducible oxide of manganese was employed.

Furthermore, Baerns, West German Patent Application No. 3,237,079.2 discloses a method for the production of ethane or ethylene by the reaction of methane and an oxygen-containing gas at a temperature between 500° C. and 900° C., at an oxygen partial pressure of less than about 0.5 atmosphere at the reactor entrance, with a ratio of methane partial pressure-to-oxygen partial pressure greater than 1 at the reactor entrance and in the presence of a solid catalyst free of acidic properties. As disclosed, the method can be performed with or without recycle of remaining unreacted methane. The highest molecular weight product formed in the disclosed method is propane, and the highest collective selectivity for the formation of ethane, ethylene and propane is only about 65% of the methane converted.

Baerns discloses that oxides of the metals of Groups III–VII of the Periodic Table are suitable for use as catalysts in the method disclosed therein and that the oxides of lead, manganese, antimony, tin, bismuth, thallium, cadmium and indium are particularly preferred. Baerns further discloses that the metal oxides can be employed with or without a carrier and that specifically preferfed carriers are alumina, silica, silicon carbide and titania. Specific examples of carrier materials disclosed were formed from gamma-alumina having BET surface areas of 160–166 m$^2$/gm, silica having a BET surface area of 290 m$^2$/gm, bismuth oxide, aluminum silicate, and titania.

OBJECTS OF THE INVENTION

It is therefore a general object of the present invention to provide a method for converting a lower molecular weight alkane to more valuable, higher molecular weight hydrocarbons which meets the aforementioned requirements and solves the aforementioned problems of prior art methods.

More particularly, it is an object of the present invention to provide a method for converting a lower molecular weight alkane to more valuable, higher molecular weight hydrocarbons with a high degree of conversion of the alkane.

It is another object of the present invention to provide a method for converting a lower molecular weight alkane to more valuable, higher molecular weight hydrocarbons with a high degree of selectivity for the production of the higher molecular weight hydrocarbons.

It is a similar object of the present invention to provide a method for converting a lower molecular weight alkane to more valuable, higher molecular weight hydrocarbons which affords a high yield of the higher molecular weight hydrocarbons.

Other objects and advantages of the present invention will become apparent upon reading the following detailed description and appended claims, and upon reference to the accompanying drawing.

SUMMARY OF THE INVENTION

These objects are achieved by an improved method for converting at least one feedstock alkane containing from 1 to 3 carbon atoms to more valuable, higher molecular weight hydrocarbons, comprising: (a) contacting the feedstock alkane containing from 1 to 3 carbon atoms with an oxygen-containing gas in a reactor in the presence of an oxidative coupling catalyst at a temperature in the range of from about 600° C. to about 1000° C., to thereby produce a gaseous mixture comprising any remaining unreacted feedstock alkane and oxygen and saturated and unsaturated aliphatic hydrocarbon products having higher molecular weights than the feedstock alkane from which they were formed; and (b) contacting the resulting gaseous mixture with an oxidative dehydrogenation catalyst under oxidative dehydrogenation conditions to thereby dehydrogenate the saturated aliphatic hydrocarbon product and produce a gaseous mixture comprising any remaining unreacted feedstock alkane and oxygen and unsaturated aliphatic hydrocarbon product.

BRIEF DESCRIPTION OF THE DRAWING

For a more complete understanding of this invention, reference should now be made to the embodiments illustrated in greater detail in the attached drawing and described below by way of examples of the invention. In the drawing.

Figure 1:
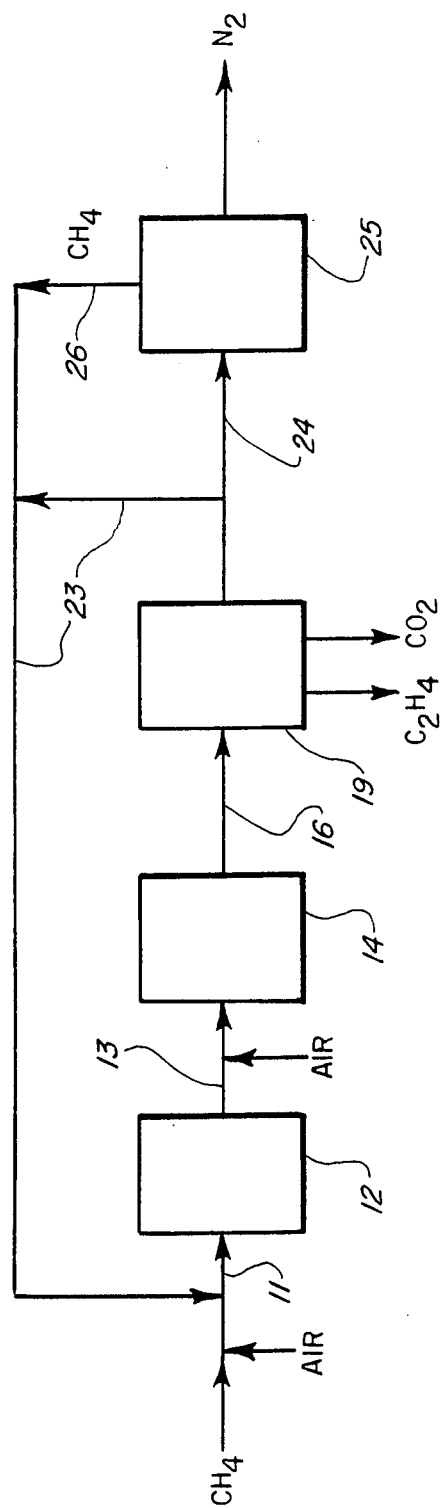
FIG. 1 is a schematic illustration of a preferred embodiment of the present invention in which: (a) a methane feedstock is combined with air in the presence of a catalyst and is initially partially converted to a mixture comprising ethane and ethylene; (b) air is introduced into the resulting product stream and the ethane in the resulting product stream is catalytically; dehydrogenated to form ethylene (c) the unsaturated aliphatic hydrocarbons and carbon dioxide in the product stream from step (b) are separated from the product mixture; (d) after separation of a slip stream from the remaining product mixture, the remaining product mixture is recycled to the methane feedstock for additional conversion in step (a) of remaining unreacted feedstock alkane; and (e) at least a portion of the methane component of the slip stream is separated from the slip stream and the separated methane is then recycled to step (a) for additional conversion of remaining unreacted feedstock alkane.

It should be understood that the drawing is a schematic illustration, and that in certain instances, details which are not necessary for an understanding of the present invention or which render other details difficult to perceive may have been omitted. It should be understood, of course, that the invention is not necessarily limited to the particular embodiments illustrated herein.

DETAILED DESCRIPTION OF THE DRAWING INCLUDING PREFERRED EMBODIMENTS

Turning first to FIG. 1, there is shown schematically a preferred embodiment of the method of this invention. Methane, illustrative of a feedstock comprising at least one alkane containing from 1 to 3 carbon atoms, is mixed with air, as a source of oxygen, and the resulting mixture is introduced through line 11 into a first reactor 12 where it is contacted with a suitable catalyst for the oxidative coupling of the aforesaid alkane. The effluent from the first reactor 12 is a gaseous product stream comprising carbon dioxide, nitrogen, any remaining unreacted feedstock alkane and oxygen, and ethane and ethylene, illustrative of alkane and alkene products having higher molecular weights than the feedstock alkane from which they were formed, and is mixed with air in line 13 and passed into a second reactor 14, where it is contacted with a suitable oxidative dehydrogenation catalyst under oxidative dehydrogenation conditions. The effluent from the second reactor 14 comprises carbon dioxide, nitrogen, any remaining unreacted feedstock alkane and oxygen, and ethylene, illustrative of higher molecular weight alkene products, and is passed in line 16 to a first separator 19 where carbon dioxide and the alkene product are separated from the gas stream. The gaseous effluent from the first separator 19, comprising nitrogen and any remaining unreacted feedstock alkane and oxygen, is then split into two streams. The first resulting stream is a major portion of the gaseous effluent from the first separator 19, and is recycled in line 23 as feedstock back to the first reactor 12. The second resulting stream is a minor portion of the gaseous effluent from the first separator 19, has the same composition as the aforesaid first resulting stream, but is passed in line 24 through a second separator 25 where at least a portion of its methane components is removed therefrom and recycled through line 26 and line 23 as feedstock back to the first reactor 12.

It should be understood that FIG. 1 illustrates merely one preferred embodiment of the method of this invention and that the present invention is not limited to the particular embodiment illustrated in FIG. 1.

Generally, a suitable feedstock for the method of this invention comprises at least one of methane, ethane and propane, preferably comprises methane and more preferably comprises a mixture of methane and ethane. Thus, a suitable feedstock for the method of this invention comprises natural gas, gases formed during mining operations, in petroleum processes or in the above- or below-ground gasification or liquefaction of coal, tar sands, oil shale and biomass.

The oxygen-containing gas for use in the method of this invention can vary in molecular oxygen content from that of air to oxygen gas itself. Air or enriched air is a preferred source of molecular oxygen. The oxygen-containing gas should provide a gas-vapor effluent mixture from the oxidative coupling reactor containing (measured on a solid-free basis) from about 2 to about 8 volume percent of oxygen, in order to avoid the flammability limits in such mixture.

The oxidative coupling reaction is performed at a temperature in the range of from about 600° C. to about 1000° C., preferably in the range of from about 700° C. to about 850° C. The oxidative coupling step of the method of this invention is performed under a total absolute pressure preferably in the range of from about 1 atmosphere to about 10 atmospheres, and more preferably in the range of from about 1 atmosphere to about 5 atmospheres. The ratio of the combined partial pressures of the feedstock alkanes containing from 1 to 3 carbon atoms in the feedstock-to-the oxygen partial pressures at the entrance of the reactor in the oxidative coupling step is preferably in the range of from about 2:1 to about 40:1 and more preferably in the range of from about 5:1 to about 30:1. The combined partial pressures of the alkanes in the feedstock containing from 1 to 3 carbon atoms at the entrance to the oxidative coupling reactor is preferably in the range of from about 0.1 to about 10 atmospheres, and more preferably in the range from about 0.2 to about 5 atmospheres. The oxygen partial pressure at the entrance to the oxidative coupling reactor is preferably in the range from about 0.01 to about 5 atmospheres and more preferably in the range of from about 0.02 to about 0.7 atmospheres. The oxygen partial pressure in the gaseous effluent from the reactor in the oxidative coupling step is preferably substantially zero.

The oxidative coupling step is performed preferably at a space velocity, calculated for a reaction pressure of one atmosphere absolute, of from about 100 to about 10,000 cubic centimeters of total feed gas comprising feedstock alkane containing from 1 to 3 carbon atoms per hour per cubic centimeter of catalyst and more preferably at a space velocity of from about 500 to about 5000 cubic centimeters of total feed gas comprising feedstock alkane containing from 1 to 3 carbon atoms per hour per cubic centimeter of catalyst. For the purposes of this definition of the space velocity, the feedstock alkane comprises from about 10 volume percent to about 80 volume percent of the total feed gas.

In one embodiment, the catalyst employed in the oxidative coupling step of the method of this invention comprises silica having a surface area less than about 175 $m^2/gm$. Preferably, the silica has a surface area of from about 5 $m^2/gm$ to about 75 $m^2/gm$. More preferably, the catalyst is silica. It is also preferred that the silica is calcined at a temperature of from about 800° C. to about 1100° C. for from about 2 hours to about 36 hours. More preferably, the silica is calcined at a temperature of from about 950° C. to about 1050° C. for from about 4 hours to about 16 hours.

In another embodiment, the catalyst employed in the oxidative coupling step of the method of this invention comprises a reducible compound of lead, antimony, vanadium, germanium, tin, bismuth, cadmium, indium, manganese, thallium, or a mixture thereof. Preferably, the reducible compound employed in an oxide, sulfide, sulfate, or carbonate of lead, vanadium antimony, germanium, tin, bismuth, cadmium, indium, manganese, thallium, or a mixture thereof. The oxidative coupling catalyst more preferably comprises a reducible compound of lead and most preferably comprises a lead oxide. If a reducible compound of lead is present, the presence of additional reducible compounds of other metals, such as zirconium and titanium, which themselves are not effective catalysts, serves to promote the activity of the lead compound in the oxidative coupling reaction.

Preferably, the oxidative coupling catalyst employed in the method of this invention comprises, in addition to the aforesaid reducible metal compound, an amorphous refractory inorganic oxide support comprising an oxide of an element from Groups IIA, IIIA, IIIB, IVA or IVB of the Periodic Table. More preferably, the amorphous refractory inorganic oxide support of the oxidative coupling catalyst employed in the method of this invention comprises silica, alumina, silica-alumina, silica-stabilized alumina, phosphated alumina, silica-stabilized phosphated alumina, aluminia-aluminum phosphate, boria-alumina, magnesia-alumina, boria, magnesia, or titania. Such amorphous refractory inorganic oxide support preferably comprises silica having a surface area preferably in the range of from about 1 $m^2/gm$ to about 175 $m^2/gm$, and more preferably in the range of from about 5 $m^2/gm$ to about 75 $m^2/gm$. More preferably the support is silica.

The reducible compound component of the oxidative coupling catalyst employed in the method of this invention comprises preferably from about 2 weight percent to about 50 weight percent of the oxidative coupling catalyst, and more preferably from about 10 weight percent to about 30 weight percent of the oxidative coupling catalyst, calculated as the reducible metal oxide and based on the total weight of the oxidative coupling catalyst.

The oxidative coupling catalyst preferably employed in the method of this invention can be prepared by impregnation of the aforesaid amorphous refractory inorganic oxide support with at least one precursor of the reducible metal compound. Any convenient, conventional impregnation technique can be employed for this purpose. For example, a soluble compound of the metal of the reducible metal oxide can be added to a sol or gel of the amorphous refractory inorganic oxide. This composition is then thoroughly blended into the sol or gel mixture, and subsequently co-gelled by the addition of a dilute ammonia solution. The resulting co-gelled material is then dried. In another method of preparation, the refractory inorganic oxide is gelled, dried, and cooled and the resulting material is then impregnated with one or more solutions of a soluble compound of the metal of the reducible metal oxide. Preferably, as will be described hereinbelow, the support containing the reducible metal compound or precursor thereof is calcined, regardless of the method of preparation used. In such case, the calcination conditions are preferably calcining at a temperature in the range of from about 500° C. to about 1050° C. for from about 2 hours to about 36 hours and more preferably calcining in air at a temperature of from about 950° C. to about 1050° C. for from about 4 hours to about 20 hours. More preferably, the support is calcined prior to incorporating the reducible metal compound or its precursor therein, and in such case, the calcination conditions employed are as described hereinabove for the calcination of silica.

It has been found that the selectivity of the oxidation coupling for the formation of coupled products can be increased by the additional incorporation thereinto of an alkali metal component into the support. The presence of the alkali metal component in the oxidative coupling catalyst also permits the concentration of the reducible metal component in the catalyst to be reduced without decreasing the selectivity of the catalyst for the formation of coupled products. Preferably, the metal of the alkali metal component is sodium, potassium or lithium. The alkali metal component is present in the catalyst at a concentration of preferably from about 0.1 to about 6 weight percent, more preferably from about 0.5 to about 3 weight percent, calculated as the alkali metal oxide and based on the weight of the catalyst. A compound of the alkali metal can be deposited by any convenient, conventional technique such as impregnation or spray drying, before, during or after deposition of the metal of the reducible metal component on the catalyst support. Upon calcination, the alkali metal component is converted to the form of its metal oxide.

The gaseous mixture resulting from the oxidative coupling reaction comprises any remaining unreacted feedstock alkane and oxygen and saturated and unsaturated aliphatic hydrocarbon products having higher molecular weights than the feedstock alkane from which they were formed. In addition, if air is employed as the source of molecular oxygen in the oxidative coupling step of the method of the present invention, the effluent from the oxidative coupling step also contains nitrogen and carbon dioxide.

In order to increase the conversion of the feedstock alkane in the oxidative coupling step and the yield of the desired products therefrom, it is desirable to recycle the unconverted feedstock alkane to the oxidative coupling step in a preferred embodiment of the method of this invention. However, recycle of the entire gaseous product mixture from the oxidative coupling reaction to the oxidative coupling step results in a decrease of both the selectivity for the formation of coupled products and the yield of coupled products. Although the presence of saturated coupled products such as ethane in the feed to the oxidative coupling reaction and, hence, in the product mixture recycled to the oxidative coupling reaction affords a surprising increase in the selectivity for both the formation of coupled products and the yield of coupled products in the oxidative coupling step, the presence of unsaturated coupled products such as ethylene and acetylene in the feed to the oxidative coupling reaction and, hence, in the recycled product mixture, has a substantial deleterious effect on the selectivity for the formation of and yield of coupled products in the oxidative coupling step. Thus, in order to increase the conversion of the feedstock alkane and yield of the desired products therefrom, the recycled gaseous mixture must be relatively free of unsaturated coupled products. Thus, in the method of this invention, if the gaseous product mixture from the oxidative coupling reaction is recycled, the unsaturated coupled products should be removed therefrom.

In the method of this invention, the gaseous mixture from the oxidative coupling step is contacted in a second reactor with an oxidative dehydrogenation catalyst under oxidative dehydrogenation conditions in order to dehydrogenate saturated coupled products to unsaturated aliphatic hydrocarbons. The oxidative dehydrogenation conditions include a temperature preferably in the range of from about 500° C. to about 900° and more preferably in the range of from about 600° C. to about 850° C. The oxidative dehydrogenation conditions also include a total absolute pressure preferably in the range of from about 1 atmosphere to about 10 atmospheres and more preferably in the range of from about 1 atmosphere to about 5 atmospheres. The oxidative dehydrogenation conditions also include a space velocity, calculated for a reaction pressure of one atmosphere absolute, preferably in the range of from about 100 to about 10,000 cubic centimeters of the gaseous mixture per hour per cubic centimeter of the oxidative dehydrogenation catalyst and more preferably in the range of from about 500 to about 5,000 cubic centimeters of the gaseous mixture per hour per cubic centimeter of the oxidative dehydrogenation catalyst.

The ratio of the partial pressure of the saturated aliphatic hydrocarbon product in the gaseous mixture from the oxidative coupling reaction-to-oxygen partial pressure at the entrance to the oxidative dehydrogenation reactor is preferably in the range of from about 40 to about 2 and more preferably in the range of from about 20 to about 5. If necessary or desirable, oxygen-containing gas is added to the gaseous mixture from the oxidative coupling reaction to bring the oxygen partial pressure at the entrance to the oxidative dehydrogenation reactor to this level.

The oxidative dehydrogenation catalyst comprises an amorphous refractory inorganic oxide comprising an oxide of Group IIA, IIIA, IIIB, IVA, or IVB of the Periodic Table or mixtures thereof. Preferably, this catalyst comprises silica, alunina or mixtures thereof. Preferably, the oxidative dehydrogenation catalysts additionally comprises a metal component wherein the metal is lead, bismuth, antimony, germanium, tin, indium, thallium or a transition metal such as vanadium, cadmium, manganese, copper, cobalt, nickel, molybdenum or chromium. The metal is preferably in the form of its oxide, sulfide, sulfate, or carbonate. More preferably, the metal component is lead oxide. In general, any aforesaid oxidative coupling catalyst can also be employed as the oxidative dehydragenation catalyst. Preparation methods described hereinabove for the oxidative coupling catalyst can also be employed to prepare the oxidative dehydrogenation catalyst.

The gaseous mixture resulting from the oxidative dehydrogenation reaction comprises any remaining unreacted feedstock alkane and oxygen and an unsaturated aliphatic hydrocarbon product having a higher molecular weight than the feedstock alkane. In addition, if air is a source of oxygen for the oxidative coupling reaction or the oxidative dehydrogenation reaction, this gaseous mixture also comprises nitrogen and carbon dioxide.

Prior to recycling the unreacted feedstock alkane component of this mixture to the oxidative coupling step, the desired unsaturated products are separated from it. This can be effected using any convenient, conventional method. One highly effective, novel technique involves passing the mixture through a charcoal bed. The unreacted feedstock alkane, oxygen and, if present, nitrogen pass through the charcoal bed faster than do the unsaturated hydrocarbon products and, if present, carbon dioxide, and are recycled to the oxidative coupling step before the unsaturated hydrocarbon products, and, if present, carbon dioxide, saturate and emerge from the bed. When the bed becomes saturated with the products and, if present, carbon dioxide, the products and, if present, carbon dioxide, begin to emerge from the bed, and the bed is removed from service and replaced in service by a fresh charcoal bed. The unsaturated hydrocarbon products and, if present, carbon dioxide are then removed from the saturated bed and the unsaturated hydrocarbon products are collected.

The adsorption or saturation step is conducted at a lower temperature than the desorption or product-removal step. The gases enter the charcoal bed at a temperature, for example, below about 60° C. at substantially atmospheric pressure absolute. Under these conditions as much as 20–30 percent of the weight of the bed is covered by adsorbed product. When the bed can hold no more adsorbed material, as shown by the presence of unsaturated hydrocarbons and, if present, carbon dioxide in the effluent gas from the charcoal bed, the feed gas is stopped and superheated steam is passed into the bed. As the bed heats up it desorbs the adsorbed hydrocarbons and, if present, carbon dioxide which pass out of the bed with excess steam. When the bed has been heated to some temperature preferably in the range of 100°–150° C. and desorption of unsaturated hydrocarbons and, if present, carbon dioxide has diminished substantially, the charcoal bed is cooled down and then returned to service. In the alternative, it has been advantageous when such beds become saturated with unsaturated hydrocarbon products and, if present, carbon dioxide, to remove the adsorbed materials by evacuating the bed. With progressive evacuation down to 29 inches of mercury vacuum, carbon dioxide, if present, and the unsaturated hydrocarbon product are removed selectively and sequentially, thus permitting an effective separation of such materials. As a third alternative for desorption, the bed can be heated and evacuated simultaneously or in sequence. In this mode, both milder heating below 100° C. and milder evacuation below about 20 inches of mercury vacuum can be used. Any oleophilic charcoal works well as do certain hydrophobic clays. In particular, coconut and bituminous charcoal have been shown to be both highly effective and inexpensive.

When the oxygen-containing gas comprises air, the gaseous mixture which remains after the step of recovering the unsaturated hydrocarbon product comprises nitrogen and, unless removed in the first separation step, carbon dioxide in addition to remaining unreacted feedstock alkane and oxygen. Thus, unless removed, nitrogen and carbon dioxide would build up in the recycled portion of the feed to the oxidative coupling step. This buildup of nitrogen and, unless removed in the first separation step, carbon dioxide in the recycle to the oxidative step can be eliminated conveniently by separating a slip stream from the recycle gas and venting a small portion, for example, 10 percent, of the recycle gas before the recycle gas is returned to the oxidative coupling step. However, in addition to nitrogen and, unless removed in the first separation step, carbon dioxide, the gas vented also contains some unreacted feedstock alkane. In order to maximize the conversion of the feedstock alkane to coupled products, it is desirable to separate the unreacted feedstock alkane component from the slip stream before it is vented and recycle the separated feedstock alkane to the oxidative coupling step. This separation can be effected by any convenient, conventional technique. One highly effective, novel technique involves passing the slip stream through a second charcoal bed. The nitrogen passes through the charcoal bed faster than do the unreacted feedstock alkane and, unless removed in the first separation step, carbon dioxide and is vented before the unreacted feedstock alkane and, carbon dioxide saturate and emerge from the bed. When the bed becomes saturated with feedstock alkane and, unless removed in the first separation step, carbon dioxide, the feedstock alkane and carbon dioxide begin to emerge from the bed, the bed is removed from service and replaced in service by a fresh charcoal bed. The unreacted feedstock alkane and, unless removed in the first separation step, carbon dioxide are then removed from the saturated bed, and the unreacted feedstock alkane is recycled to the oxidative coupling step.

For reclaiming unreacted feedstock alkane from the slip stream, a somewhat different mode of operating the charcoal bed is advantageous than that described hereinabove. In this case, because of the low adsorptive capacity that charcoals have for methane, it is desirable to use rapid adsorption-desorption cycles, without externally changing the temperature of the bed. It has been advantageous when such beds become saturated with methane and carbon dioxide (the nitrogen having been discharged) at a temperature up to 60° C. and substantially atmospheric pressure absolute. To remove adsorbed methane by evacuating the bed. With progressive evacuation down to about 28–29 inches of mercury vacuum, methane and carbon dioxide are removed selectively and sequentially, thus permitting an effective separation of such components. Methane is then returned to the recycle system; while carbon dioxide is selectively rejected.

The present invention will be more clearly understood from the following specific examples.

EXAMPLES 1–149

Examples 1–149 demonstrate significant parameters of the oxidative coupling reaction of the method of this invention. In each of Examples 1–149, a stream of methane and air was passed through a heated quartz tube (except Examples 28–31 where a ceramic reactor was used) having an inside diameter of 1.43 centimeters and a length of from 10 to 43 centimeters and, in all cases except Examples 1–4 and 28–31, whose internal volume in the middle of the tube was filled with solid particles or pellets. The reaction pressure was approximately one atmosphere absolute. The product gas effluent from the tube was cooled with an ice bath condenser and analyzed. The experimental parameters employed in Examples 1–149 and the results therefrom are presented in Tables 1–19. In all cases except Examples 1–4 and 28–31, the units of space velocity are the volume (in cubic centimeters) of the combination of methane and air fed to the reactor per hour per cubic centimeter of catalyst in the tube. In Examples 1–4 and 28–31, the space velocity is the volume (in cubic centimeters) of the combination of methane and air fed to the reactor per hour per the inside volume (in cubic centimeters) of the reactor. Each of the product selectivity, selectivity for the formation of coupled products ($C_2+$) and yield of $C_2+$ (the product of methane conversion multiplied by the selectivity for the formation of $C_2+$ divided by 100) is reported as mole percent of the carbon in methane in the feed that is converted. $C_4+$ in the tables refers to gaseous products containing at least 4 carbon atoms.

In Examples 1–4, the quartz tube was empty, and very little oxygen was consumed even at the highest reaction temperature, leading to little consumption of methane. However, the selectivity for the formation of coupled products ($C_2+$), based on the amount of methane consumed, was substantial even though most oxides of carbon appeared as carbon monoxide.

In Examples 5–10, when the tube was filled with pellets of Calsicat D (a product of Mallinckrodt, Inc. of Erie, Pa.), a preferred silica support for the preferred oxidative coupling catalyst, when a reaction temperature of at least 850° C. was employed, nearly all oxygen was consumed, and product selectivity for the formation of coupled product was moderate at 53%. The conversion to coupled products increased as the reaction temperature was increased, with ethylene predominating as the coupled product. The selectivity for the formation of coupled products also increased at a given reaction temperature as the $CH_4/O_2$ mole ratio increased.

When ceramic alumina chips were employed as the tube packing, as indicated in Table 3, for Examples 11–13, oxygen consumption was less, but selectivity for the formation of coupled products ($C_2+$) was appreciably better (67–88%) than when Calsicat D was employed as the tube packing. However, high temperatures of the order of 890°–945° C. were required to increase oxygen consumption, at which temperature methane reforming, as evidenced by CO formation, increased substantially.

A tube packing of 1 percent by weight of potassium bromide on Calsicat D silica (the silica was dispersed in an aqueous solution of potassium bromide; the solution was evaporated; and the silica was then dried and calcined) was employed in Examples 14–17 (Table 4) and was approximately as active and selective as Calsicat D alone. Celite 408, a diatomaceous silica and a product of Johns-Mannville Company, was employed as the tube packing in Examples 18–21 (Table 5) and afforded relatively poor selectivity. Zirconia containing 2 percent by weight of alumina was employed as the tube packing in Examples 22–25 (Table 6) and promoted only formation of carbon oxides. Alpha Alumina was employed as the tube packing in Example 26 (Table 6) and afforded good activity but relatively low selectivity. Mordenite (Norton Zeolon 100) was employed as the tube packing in Example 27 (Table 7) and formed little coupled product but afforded copious coking. A ceramic α-alumina tube, not containing any tube packing, was employed in Examples 28–31 (Table 7) and was somewhat active at low space velocity and high reaction temperatures and afforded high selectivities for the formation of $C_2$ and $C_3$ products. Magnesium aluminum borate, a mixed oxide, was employed as the tube packing in Examples 32–35 (Table 8) and was only moderately active and afforded only moderate selectivity for the formation of coupled products.

In Examples 36–49, several forms of tube packings of lead oxide on various supports were employed. In Examples 36–38 (Table 9), lead oxide on α-alumina having a surface area of 31 $m^2/g$ was highly active in catalyzing the conversion of oxygen even at relatively low reaction temperatures, but with relatively poor selectivities of 44–55% for the production of coupled products. By contrast, a low surface area silica (Examples 39–40) was highly selective.

TABLE 1

| | Example | | | |
|---|---|---|---|---|
| | 1 | 2 | 3 | 4 |
| Tube Packing | Empty Tube | | | |
| Reactor Temp. (°C.) | 700 | 800 | 850 | 900 |
| Space Velocity | 480 | 480 | 480 | 480 |
| $CH_4/O_2$ (mole ratio) | 9.7/1 | 9.7/1 | 9.7/1 | 9.7/1 |
| $O_2$ Conversion (mole %) | 0.2 | 4 | 12 | 29 |
| $CH_4$ Conversion (mole %) | — | 0.4 | 1.7 | 4.5 |
| Product Selectivity | | | | |
| CO | 0 | 24 | 34 | 41 |
| $CO_2$ | 0 | 0 | 0 | 3 |
| $C_2H_4$ | 0 | 32 | 35 | 39 |
| $C_2H_6$ | 100 | 44 | 31 | 16 |
| $C_2H_2$ | — | — | — | — |
| $C_3$'s | — | — | — | — |
| $C_4$'s+ | — | — | — | — |
| Selectivity to $C_2$+ | 100 | 76 | 66 | 55 |
| Yield of $C_2$+ | nil | 0.3 | 1.1 | 2.5 |

TABLE 2

| | Example | | | | | |
|---|---|---|---|---|---|---|
| | 5 | 6 | 7 | 8 | 9 | 10 |
| Tube Packing | Calsicat D Silica | | | | | |
| Reactor Temp. (°C.) | 700 | 800 | 850 | 900 | 900 | 800 |
| Space Velocity | 1200 | 1200 | 1200 | 1200 | 1000 | 1000 |
| $CH_4/O_2$ (mole ratio) | 9.6/1 | 9.6/1 | 9.6/1 | 9.6/1 | 27/1 | 27/1 |
| $O_2$ Conversion (mole %) | 4.6 | 49 | 94 | 98+ | 97+ | 97+ |
| $CH_4$ Conversion (mole %) | 0.1 | 4.7 | 10 | 12 | 5.5 | 4.1 |
| Product Selectivity | | | | | | |
| CO | 78 | 44 | 25 | 22 | 19 | 35 |
| $CO_2$ | 20 | 20 | 23 | 22 | 15 | 19 |
| $C_2H_4$ | 0 | 16 | 37 | 51 | 62 | 25 |
| $C_2H_6$ | 2 | 20 | 16 | 5 | 4 | 22 |
| $C_2H_2$ | — | — | — | — | — | — |
| $C_3$'s | — | — | — | — | — | — |
| $C_4$'s+ | — | — | — | — | — | — |
| Selectivity to $C_2$+ | 2 | 36 | 53 | 56 | 66 | 47 |
| Yield of $C_2$+ | nil | 1.7 | 5.3 | 6.7 | 3.6 | 1.9 |

TABLE 3

| | Example | | |
|---|---|---|---|
| | 11 | 12 | 13 |
| Tube Packing | Ceramic Chips | | |
| Reactor Temp. (°C.) | 851 | 889 | 945 |
| Space Velocity | 1696 | 1696 | 1696 |
| $CH_4/O_2$ (mole ratio) | 24/1 | 24/1 | 24/1 |
| $O_2$ Conversion (mole %) | 14.3 | 4.1 | 57 |
| $CH_4$ Conversion (mole %) | 0.4 | 0.6 | 3.9 |
| Product Selectivity | | | |
| CO | — | 3 | 26 |
| $CO_2$ | 29 | 9 | 7 |
| $C_2H_4$ | 10 | 27 | 25 |
| $C_2H_6$ | 60 | 58 | 37 |
| $C_2H_2$ | — | — | — |
| $C_3$'s | — | — | — |
| $C_4$'s | — | — | — |
| Selectivity to $C_2$+ | 71 | 88 | 67 |
| Yield of $C_2$+ | 0.3 | 0.5 | 2.6 |

TABLE 4

| | Example | | | |
|---|---|---|---|---|
| | 14 | 15 | 16 | 17 |
| Tube Packing | 1% KBr/Calsicat D Silica | | | |
| Reactor Temp. (°C.) | 700 | 800 | 850 | 900 |
| Space Velocity | 1200 | 1200 | 1200 | 1200 |
| $CH_4/O_2$ (mole ratio) | 10/1 | 10/1 | 10/1 | 10/1 |
| $O_2$ Conversion (mole %) | 81 | 98+ | 98+ | 98+ |
| $CH_4$ Conversion (mole %) | 6.9 | 13 | 14 | 16 |
| Product Selectivity | | | | |
| CO | 67 | 34 | 24 | 20 |
| $CO_2$ | 18 | 16 | 22 | 21 |
| $C_2H_4$ | 7 | 34 | 38 | 48 |
| $C_2H_6$ | 9 | 15 | 13 | 6 |
| $C_2H_2$ | 0 | 0 | 0 | 0 |
| $C_3$'s | 0 | 2 | 3 | 4 |
| $C_4$'s | — | — | — | — |
| Selectivity to $C_2$+ | 16 | 51 | 54 | 58 |
| Yield of $C_2$+ | 1.1 | 6.6 | 7.6 | 9.3 |

TABLE 5

| | Example | | | |
|---|---|---|---|---|
| | 18 | 19 | 20 | 21 |
| Tube Packing | Celite 408 | | | |
| Reactor Temp. (°C.) | 700 | 800 | 850 | 900 |
| Space Velocity | 1200 | 1200 | 1200 | 1200 |
| $CH_4/O_2$ (mole ratio) | 10/1 | 10/1 | 10/1 | 10/1 |
| $O_2$ Conversion (mole %) | 42 | 97+ | 98+ | 98+ |
| $CH_4$ Conversion (mole %) | 3.2 | 6.8 | 7.2 | 8.0 |
| Product Selectivity | | | | |
| CO | 53 | 61 | 64 | 63 |
| $CO_2$ | 35 | 31 | 26 | 23 |
| $C_2H_4$ | 0 | 3 | 5 | 10 |

TABLE 5-continued

|  | Example |  |  |  |
|---|---|---|---|---|
|  | 18 | 19 | 20 | 21 |
| $C_2H_6$ | 13 | 5 | 5 | 4 |
| $C_2H_2$ | 0 | 0 | 0 | 0 |
| $C_3$'s | 0 | 0 | 0 | 0 |
| $C_4$'s | — | — | — | — |
| Selectivity to $C_2^+$ | 13 | 8 | 10 | 14 |
| Yield of $C_2^+$ | 0.4 | 0.5 | 0.7 | 1.1 |

TABLE 6

|  | Example |  |  |  |  |
|---|---|---|---|---|---|
|  | 22 | 23 | 24 | 25 | 26 |
| Tube Packing | $ZrO_2$ + 2% $Al_2O_3$ | | | | α-Alumina |
| Reactor Temp. (°C.) | 700 | 800 | 850 | 850 | 800 |
| Space Velocity | 4800 | 4800 | 4800 | 1200 | 8700 |
| $CH_4/O_2$ (mole ratio) | 2/1 | 2/1 | 2/1 | 10/1 | 19.5/1 |
| $O_2$ Conversion (mole %) | 100 | 100 | 100 | 100 | 100 |
| $CH_4$ Conversion (mole %) | 26 | 28 | 33 | 11 | — |
| Product Selectivity | | | | | |
| CO | 20 | 28 | 35 | 64 | 50.4 |
| $CO_2$ | 81 | 72 | 65 | 36 | 34.5 |
| $C_2H_4$ | 0 | 0 | 0 | 0 | 7.2 |
| $C_2H_6$ | 0 | 0 | 0 | 0 | 15.6 |
| $C_2H_2$ | 0 | 0 | 0 | 0 | — |
| $C_3$'s | 0 | 0 | 0 | 0 | 0.6 |
| $C_4$'s | — | — | — | — | — |
| Selectivity to $C_2^+$ | 0 | 0 | 0 | 0 | 23 |
| Yield of $C_2^+$ | 0 | 0 | 0 | 0 | — |

TABLE 7

|  | Example |  |  |  |  |
|---|---|---|---|---|---|
|  | 27 | 28 | 29 | 30 | 31 |
| Tube Packing | Mordenite | Empty Ceramic Reactor | | | |
| Reactor Temp. (°C.) | 833 | 840 | 885 | 937 | 915 |
| Space Velocity | 8700 | 1696 | 1696 | 1696 | 848 |
| $CH_4/O_2$ (mole ratio) | 20/1 | 24.1/1 | 24.1/1 | 24.1/1 | 29.1/1 |
| $O_2$ Conversion (mole %) | 92.5 | 3.8 | 7.4 | 19.7 | 43.2 |
| $CH_4$ Conversion (mole %) | 4.4 | nil | 0.5 | 1.8 | 4.1 |
| Product Selectivity | | | | | |
| CO | 51.9 | — | — | 19.3 | 22.7 |
| $CO_2$ | 43.9 | — | — | — | 0.6 |
| $C_2H_4$ | — | 92.2 | 20.4 | 33.6 | 29.1 |
| $C_2H_6$ | 4.2 | — | 64.8 | 33.9 | 35.6 |
| $C_2H_2$ | — | — | — | — | — |
| $C_3$'s | — | 7.8 | 14.8 | 11.8 | 8.3 |
| $C_4$'s$^+$ | — | — | — | 1.4 | 3.7 |
| Selectivity to $C_2^+$ | 4.2 | 100 | 100 | 80.7 | 76.7 |
| Yield of $C_2^+$ | 0.18 | nil | 0.5 | 1.5 | 3.1 |

TABLE 8

|  | Example |  |  |  |
|---|---|---|---|---|
|  | 32 | 33 | 34 | 35 |
| Tube Packing | Magnesium Aluminum Borate | | | |
| Reactor Temp. °C. | 811 | 851 | 846 | 845 |
| Space Velocity | 1695 | 1695 | 848 | 424 |
| $CH_4/O_2$ (mole ratio) | 22.6/1 | 22.6/1 | 24.9/1 | 30.1/1 |
| $O_2$ Conversion (mole %) | 39.9 | 38.0 | 63.4 | 98.0 |
| $CH_4$ Conversion (mole %) | 2.2 | 3.2 | 3.8 | 3.4 |
| Product Selectivity | | | | |
| CO | 46.7 | 48.7 | 40.2 | 49.1 |
| $CO_2$ | 12.4 | 5.4 | 7.6 | 8.0 |
| $C_2H_4$ | 6.0 | 10.5 | 19.3 | 22.3 |
| $C_2H_6$ | 28.6 | 28.2 | 25.3 | 15.6 |
| $C_2H_2$ | — | 4.6 | 3.5 | 1.7 |
| $C_3$'s | 2.2 | 1.6 | 3.2 | 2.8 |
| $C_4$'s | 4.2 | 1.0 | 1.0 | 0.4 |
| Selectivity to $C_2^+$ | 41.0 | 45.9 | 52.3 | 42.8 |
| Yield of $C_2^+$ | 0.9 | 1.5 | 2.0 | 1.5 |

Examples 39–49 (Table 9) demonstrate the surprising influence on the oxidative coupling reaction of the physical properties of the support employed in the lead oxide catalyst. By contrast to the relatively high surface area supports employed in Examples 47–49, lead oxide on Calsicat D, a low surface area silica, afforded very high conversion of oxygen in all cases, with selectivities for the formation of coupled products in excess of 90% at $CH_4/O_2$ mole ratios of at least 19/1. Furthermore, in such examples, the selectivities for the formation of coupled products were maintained at levels of greater than 75% even at the $CH_4/O_2$ ratio of 5/1. The high surface area silica tube packing employed in Examples 47–49 afforded selectivities for the formation of coupled products that were comparable to those for the α-alumina packing employed in Examples 36–38.

To establish the influence of the surface are of the support used in preparing the oxidative coupling catalyst and of the conditions under which such support is calcined prior to impregnation, several samples of a high surface area silica (Philadelphia Quartz PQ-CD107G $SiO_2$) with a surface area of 239 m$^2$/gm were calcined under various conditions (indicated in Table 10), converted to catalysts, each containing 20% by weight of PbO, by precipitation of a lead compound from an aqueous solution of its nitrate in the presence of the silica and further calcination in air at about 600° C. to form the PbO-impregnated silica, and then evaluated as catalysts in the oxidative coupling reaction in Examples 50–54. In each evaluation, the following conditions were employed: a reaction temperature of 750°–850° C., a space velocity of 6600 cc/hr/cc, and a $CH_4/O_2$ mole ratio of 20. The experimental parameters and results presented in Table 10 for Examples 50–54 illustrate that, as the surface area of the silica is decreased, until the surface area fell to about 21 m$^2$/gm, there was a progressive increase in the selectivity for the production of coupled products.

TABLE 9

|  | Example | | | | | | | | | | | | | |
|---|---|---|---|---|---|---|---|---|---|---|---|---|---|---|
|  | 36 | 37 | 38 | 39 | 40 | 41 | 42 | 43 | 44 | 45 | 46 | 47 | 48 | 49 |
| Tube Packing | αAlumina | | | 20% PbO on Calsicat D Silica (245 m$^2$/g) | | | | | | | | 17% PbO on High Surface Area Silica (245 m$^2$/g) | | |
| Reactor Temp. (°C.) | 757 | 818 | 803 | 733 | 830 | 835 | 852 | 872 | 896 | 915 | 914 | 740 | 740 | 740 |
| Space Velocity | 8700 | 8700 | 8700 | 6600 | 6600 | 3300 | 3300 | 6600 | 3300 | 1320 | 1320 | 13,040 | 6135 | 1341 |
| $CH_4/O_2$ (mole | 20/1 | 19/1 | 5.1/1 | 20/1 | 20/1 | 21/1 | 21/1 | 19/1 | 20/1 10.3/1 | 5.2/1 | 10/1 | 10/1 | 10/1 | |

TABLE 9-continued

| | Example | | | | | | | | | | | | | |
|---|---|---|---|---|---|---|---|---|---|---|---|---|---|---|
| | 36 | 37 | 38 | 39 | 40 | 41 | 42 | 43 | 44 | 45 | 46 | 47 | 48 | 49 |
| ratio) | | | | | | | | | | | | | | |
| $O_2$ Conversion (mole %) | 100 | 100 | 100 | 37.9 | 44.1 | 76.8 | 88.0 | 65.8 | 92.3 | 100 | 88.7 | 19.9 | 26.1 | 53.0 |
| $CH_4$ Conversion (mole %) | | | | | | | | 6.8 | 8.5 | 13.4 | 18.7 | | | |
| Product Selectivity | | | | | | | | | | | | | | |
| CO | — | 1.2 | — | — | — | — | — | — | — | — | 6.6 | — | — | 1.6 |
| $CO_2$ | 48.0 | 44.2 | 55.6 | 37.4 | 9.7 | 9.8 | 9.7 | 8.5 | 9.6 | 14.2 | 18.3 | 48.5 | 41.4 | 39.4 |
| $C_2H_4$ | 17.6 | 26.0 | 21.8 | 2.0 | 20.5 | 31.4 | 35.8 | 30.8 | 37.4 | 43.6 | 30.2 | 6.9 | 8.2 | 16.3 |
| $C_2H_6$ | 32.8 | 26.2 | 20.8 | 60.4 | 68.0 | 57.0 | 52.2 | 53.2 | 42.4 | 26.2 | 20.2 | 44.3 | 50.2 | 42.0 |
| $C_2H_2$ | — | — | — | — | — | — | — | 2.7 | 2.8 | 2.0 | 0.0 | — | — | — |
| $C_3$'s | 1.5 | 2.4 | 1.8 | 0.2 | 1.8 | 1.8 | 2.4 | 4.8 | 7.5 | 7.2 | 19.5 | 0.3 | 0.2 | 0.6 |
| $C_4$'s | — | — | — | — | — | — | — | — | 0.4 | 6.8 | 5.6 | — | — | — |
| Selectivity to $C_2^+$ | 51.9 | 54.6 | 44.4 | 62.6 | 90.3 | 90.2 | 90.4 | 91.5 | 90.5 | 85.8 | 75.5 | 51.5 | 58.6 | 58.9 |
| Yield of $C_2^+$ | | | | | | | | 6 | 8 | 11 | 14 | | | |

TABLE 10

| Example | Conditions of Calcination Before Impregnation | Surface Area ($m^2$/gm) | Selectivity to $C_2^+$ |
|---|---|---|---|
| 50 | 2 hrs. at 650° C. | 239 | 45 |
| 51 | 8 hrs. at 830° C. | 179 | 66 |
| 52 | 8 hrs. at 920° C. | 116 | 85 |
| 53 | 8 hrs. at 970° C. | 21 | Low Activity |
| 54 | 4 hrs. at 1000° C. | <2 | Inactive |

The catalyst prepared in Example 52 was evaluated in Examples 55–59 as a catalyst for the oxidative coupling reaction under varying conditions of reaction temperature and space velocity. As indicated by the experimental parameters and results presented for Examples 55–59 in Table 11, the degree of oxygen conversion increased as the reaction temperature was increased at a constant space velocity and as the space velocity was decreased.

To establish the influence of the presence in the catalyst of agents, such as alkali metal components which modify the characteristics of the catalyst, such as the acidity of the support, several samples of a low surface area silica (Type 16753 manufactured by Norton Company) having a surface area of 29 $m^2$/gm were calcined at 550°–600° C. with air for 2–3 hours, converted to catalysts, each containing 20% PbO by weight and either no or various amounts of a sodium or magnesium component incorporated thereinto by precipitation of a lead compound and either a sodium or magnesium compound from a solution of their nitrates in an aqueous slurry of the silica and calcination in air to form the PbO- and either $Na_2O$- or MgO-impregnated silica. These metal-impregnated silicas were then evaluated as catalysts in the oxidative coupling reaction in Examples 60–118. The experimental parameters and results obtained are presented in Tables 12–15.

The results of Example 60–118 illustrate that a catalyst can be improved to afford a substantially higher selectivity by incorporation thereinto of a relatively small amount of a sodium component. This effect is most apparent after the catalyst has been heat treated. The incorporation of relatively higher amounts of the sodium component into the catalyst affords relatively less improvement of the selectivity of the catalyst and may promote instability of the catalyst.

TABLE 11

| | Example | | | | |
|---|---|---|---|---|---|
| | 55 | 56 | 57 | 58 | 59 |
| Tube Packing | 20% PbO on 116 $m^2$/gm Silica | | | | |
| Reaction Temp. (°C.) | 748 | 795 | 849 | 839 | 856 |
| Space Velocity | 6600 | 6600 | 6600 | 3300 | 1320 |
| $CH_4/O_2$ (mole ratio) | 20.1/1 | 20.1/1 | 20.1/1 | 21.5/1 | 24.1/1 |
| $O_2$ Conversion (mole %) | 6.1 | 26.0 | 41.7 | 73.9 | 99.9 |
| Product Selectivity | | | | | |
| CO | — | — | — | — | 10.7 |
| $CO_2$ | 16.0 | 13.7 | 13.1 | 14.4 | 20.1 |
| $C_2H_4$ | 8.8 | 8.8 | 18.2 | 28.8 | 33.4 |
| $C_2H_6$ | 51.8 | 60.0 | 56.8 | 47.9 | 34.4 |
| $C_2H_2$ | — | — | — | — | — |
| $C_3$'s | 5.1 | 5.1 | 4.8 | 4.2 | 1.5 |
| $C_4$'s | 18.4 | 12.4 | 7.2 | 4.8 | — |
| Selectivity to $C_2^+$ | 84.1 | 86.3 | 87.0 | 85.7 | 69.3 |

TABLE 12

| | Example | | | |
|---|---|---|---|---|
| | 60 | 61 | 62 | 63 |
| Tube Packing | 20% PbO—Norton $SiO_2$ Containing 0% $Na_2O$ | | | |
| Reaction Temp. (°C.) | 622 | 730 | 799 | 850 |
| Space Velocity | 1700 | 1700 | 1700 | 1700 |
| $CH_4/O_2$ (mole ratio) | 24.0 | 24.0 | 24.0 | 24.0 |
| $O_2$ conversion (mole %) | 42.7 | 99.2 | 99.2 | 99.2 |
| $CH_4$ conversion (mole %) | (1) | 3.2 | 3.8 | 5.0 |
| Product Selectivity | | | | |
| $H_2$ | (1) | — | — | — |
| CO | (1) | 21.8 | 26.9 | 22.9 |
| $CO_2$ | (1) | 50.7 | 38.5 | 25.1 |
| $C_2H_4$ | (1) | 6.3 | 13.8 | 20.7 |
| $C_2H_6$ | (1) | 19.8 | 17.4 | 18.7 |
| $C_2H_2$ | (1) | — | — | 0.5 |
| $C_3H_8$ | (1) | 1.3 | 0.6 | 1.0 |
| $C_3H_6$ | (1) | 1.3 | 0.6 | 1.0 |
| i-$C_4$ | (1) | — | — | — |
| n-$C_4$ | (1) | — | — | — |
| i-$C_4$ = | (1) | — | — | 2.5 |
| Unidentified $C_4$ | (1) | — | 2.9 | 8.6 |
| Benzene | (1) | — | — | — |
| Selectivity to $C_2^+$ | (1) | 27.4 | 34.7 | 52.0 |
| Yield of $C_2^+$ | (1) | 0.88 | 1.32 | 2.60 |
| $C_2H_4/C_2H_6$ (mole ratio) | 0 | 0.321 | 0.793 | 1.112 |

(1) Conversion was too low to obtain accurate selectivity measurements.

TABLE 13

| Example |
|---|

TABLE 13-continued

| | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|
| Tube Packing | 20% PbO—Norton SiO$_2$ Containing 0.67% Na$_2$O | | | | | | | | | | | | | | | | |
| Reaction Temp. (°C.) | 566 | 609 | 633 | 674 | 714 | 770 | 784 | 816 | 840 | 853 | 850 | 847 | 851 | 845 | 861 | 865 | 855 |
| Space Velocity | 1696 | 1696 | 1696 | 1696 | 1696 | 1696 | 1696 | 1696 | 1696 | 1696 | 1696 | 3300 | 3390 | 3390 | 3390 | 3390 | 3390 |
| CH$_4$/O$_2$ (mole ratio) | 33.3 | 33.3 | 33.3 | 33.3 | 33.3 | 33.3 | 30.6 | 30.6 | 30.6 | 30.6 | 30.6 | 24.5 | 24.5 | 24.8 | 24.8 | 24.8 | 24.8 |
| O$_2$ conversion (mole %) | 85.1 | 98.8 | 99.3 | 98.7 | 99.5 | 99.3 | 99.5 | 99.3 | 99.5 | 99.4 | 99.5 | 99.4 | 99.4 | 77.4 | 94.7 | 99.6 | 98.9 |
| CH$_4$ conversion (mole %) | 1.3 | 2.3 | 2.5 | 3.5 | 4.6 | 4.5 | 5.0 | 6.1 | 6.0 | 6.3 | 6.2 | 6.8 | 6.1 | 5.5 | 6.5 | 7.4 | 7.8 |
| Product Selectivity | | | | | | | | | | | | | | | | | |
| H$_2$ | — | — | — | — | — | — | — | — | — | 11.0 | 10.9 | 8.1 | 1.7 | — | — | 2.0 | 6.7 |
| CO | — | — | — | — | — | — | 3.7 | 1.1 | 3.0 | 2.8 | 3.7 | 5.2 | 3.4 | 2.5 | 2.5 | 2.9 | 2.7 |
| CO$_2$ | 89.5 | 60.9 | 53.5 | 42.6 | 47.2 | 42.6 | 18.8 | 13.9 | 9.7 | 11.7 | 10.6 | 12.5 | 12.5 | 13.0 | 10.4 | 12.1 | 10.6 |
| C$_2$H$_4$ | — | 6.3 | 11.7 | 21.6 | 29.5 | 30.7 | 24.0 | 30.8 | 33.3 | 35.8 | 33.8 | 33.7 | 26.8 | 25.5 | 30.5 | 32.4 | 42.1 |
| C$_2$H$_6$ | 10.5 | 29.9 | 32.4 | 27.7 | 18.2 | 10.9 | 49.5 | 48.1 | 47.1 | 42.5 | 44.3 | 41.3 | 51.6 | 54.0 | 51.3 | 45.4 | 38.3 |
| C$_2$H$_2$ | — | — | — | — | — | — | 1.0 | 0.7 | 0.9 | 1.2 | 1.0 | 0.9 | 0.7 | 0.8 | 0.3 | 1.0 | 1.4 |
| C$_3$H$_8$ & C$_3$H$_6$ | — | 1.4 | 1.9 | 2.0 | 3.1 | 2.1 | 2.1 | 2.7 | 3.2 | 3.4 | 3.4 | 3.3 | 2.7 | 3.1 | 3.5 | 3.1 | 3.3 |
| i-C$_4$ | — | — | — | — | — | — | — | — | — | — | — | — | — | — | — | — | — |
| n-C$_4$ | — | — | 0.2 | 0.8 | 1.8 | 2.8 | 0.4 | 1.5 | 1.3 | 1.3 | 1.2 | 1.4 | 1.0 | 0.5 | 0.8 | 1.7 | 1.0 |
| 1-C$_4$ = | — | 1.5 | 0.4 | 5.3 | 0.1 | 0.1 | 0.4 | 1.1 | 1.6 | 1.3 | 1.9 | 1.7 | 1.3 | 0.5 | 0.8 | 1.3 | 0.3 |
| Unidentified C$_4$ | — | — | — | — | — | — | — | — | — | — | — | — | — | — | — | — | 0.2 |
| Benzene | — | — | — | — | — | 10.2 | — | — | — | — | — | — | — | — | — | — | — |
| Selectivity to C$_2$+ | 10.5 | 39.1 | 46.6 | 57.4 | 52.7 | 57.4 | 77.4 | 84.9 | 87.4 | 85.5 | 85.6 | 82.3 | 84.1 | 84.4 | 87.2 | 84.9 | 86.6 |
| Yield of C$_2$+ | 0.14 | 0.90 | 1.17 | 2.01 | 2.42 | 2.58 | 3.87 | 5.18 | 5.24 | 5.39 | 5.31 | 5.60 | 5.13 | 4.64 | 5.67 | 6.28 | 6.75 |
| C$_2$H$_4$/C$_2$H$_6$ (mole ratio) | 0 | 0.266 | 0.360 | 0.780 | 1.621 | 2.808 | 0.485 | 0.639 | 0.707 | 0.842 | 0.764 | 0.815 | 0.520 | 0.473 | 0.595 | 0.712 | 1.099 |

| | Example | | | | | | | | | | | | | |
|---|---|---|---|---|---|---|---|---|---|---|---|---|---|---|
| | 81 | 82 | 83 | 84 | 85 | 86 | 87 | 88 | 89 | 90 | 91 | 92 | 93 | 94 |
| Tube Packing | 20% PbO—Norton SiO$_2$ Containing 0.67 Na$_2$O | | | | | | | | | | | | | |
| Reaction Temp. (°C.) | 843 | 869 | 871 | 876 | 886 | 874 | 873 | 871 | 870 | 869 | 866 | 864 | 872 | 854 |
| Space Velocity | 3390 | 3390 | 3390 | 3390 | 3390 | 3390 | 3390 | 3390 | 3390 | 3390 | 3390 | 3390 | 3390 | 3390 |
| CH$_4$/O$_2$ (mole ratio) | 24.8 | 24.8 | 24.4 | 24.4 | 24.4 | 24.4 | 24.4 | 24.4 | 24.4 | 24.4 | 24.5 | 24.5 | 24.5 | 24.5 |
| O$_2$ conversion (mole %) | 58.0 | 88.4 | 94.1 | 94.7 | 99.5 | 86.7 | 85.2 | 82.5 | 72.9 | 70.5 | 72.3 | 63.1 | 70.9 | 57.6 |
| CH$_4$ conversion (mole %) | 4.3 | 6.7 | 6.5 | 7.2 | 7.1 | 6.4 | 6.2 | 6.1 | 5.8 | 5.9 | 4.7 | 4.5 | 5.6 | 4.5 |
| Product Selectivity | | | | | | | | | | | | | | |
| H$_2$ | — | 0.9 | 1.0 | 0.7 | 3.8 | 1.2 | 1.2 | 1.3 | 1.1 | 0.9 | — | — | 1.2 | — |
| CO | 2.0 | 2.7 | 3.6 | 3.4 | 3.8 | 3.3 | 3.1 | 3.2 | 3.2 | 2.8 | 3.5 | 2.6 | 3.0 | 2.4 |
| CO$_2$ | 11.8 | 13.4 | 9.2 | 11.6 | 8.7 | 10.5 | 9.0 | 8.7 | 10.3 | 9.9 | 9.1 | 9.1 | 8.1 | 8.7 |
| C$_2$H$_4$ | 24.7 | 31.4 | 33.7 | 35.3 | 36.9 | 32.2 | 33.0 | 31.6 | 28.0 | 31.3 | 28.3 | 28.1 | 28.2 | 27.3 |
| C$_2$H$_6$ | 56.4 | 44.8 | 47.4 | 43.5 | 41.4 | 46.8 | 48.2 | 48.0 | 46.5 | 45.8 | 53.0 | 53.9 | 47.3 | 53.2 |
| C$_2$H$_2$ | 1.1 | 0.6 | 0.5 | 1.0 | 1.1 | 0.6 | 0.9 | 0.6 | 0.7 | 0.8 | 0.7 | 0.9 | 0.9 | 0.2 |
| C$_3$H$_8$ & C$_3$H$_6$ | 3.4 | 3.6 | 3.4 | 2.9 | 3.8 | 3.3 | 3.4 | 3.2 | 2.9 | 2.7 | 3.4 | 3.3 | 3.2 | 3.5 |
| i-C$_4$ | — | — | — | — | 1.8 | 0.8 | — | 1.9 | 6.9 | 5.7 | — | 0.9 | 7.4 | 3.7 |
| n-C$_4$ | 0.3 | 1.4 | 1.0 | 1.3 | 1.5 | 1.4 | 1.3 | 1.3 | 0.8 | 0.5 | 2.1 | 0.5 | 1.2 | 0.5 |
| 1-C$_4$ = | 0.3 | 2.1 | 1.2 | 1.1 | 1.0 | 1.1 | 1.2 | 1.4 | 0.7 | 0.6 | — | 0.7 | 0.6 | 0.5 |
| Unidentified C$_4$ | — | — | — | — | — | — | — | — | — | — | — | — | — | — |
| Benzene | — | — | — | — | — | — | — | — | — | — | — | — | — | — |
| Selectivity to C$_2$+ | 86.2 | 83.9 | 87.2 | 85.1 | 87.5 | 86.2 | 88.0 | 88.0 | 86.5 | 87.4 | 87.5 | 88.3 | 88.8 | 88.9 |
| Yield of C$_2$+ | 3.71 | 5.62 | 5.67 | 6.13 | 6.21 | 5.52 | 5.46 | 5.37 | 5.02 | 5.17 | 4.11 | 3.97 | 4.97 | 4.00 |
| C$_2$H$_4$/C$_2$H$_6$ (mole ratio) | 0.437 | 0.702 | 0.712 | 0.806 | 0.893 | 0.688 | 0.684 | 0.660 | 0.602 | 0.683 | 0.533 | 0.520 | 0.596 | 0.513 |

TABLE 14

| | Example | | | | | | | | | | | | |
|---|---|---|---|---|---|---|---|---|---|---|---|---|---|
| | 95 | 96 | 97 | 98 | 99 | 100 | 101 | 102 | 103 | 104 | 105 | 106 | 107 |
| Tube Packing | 20% PbO—Norton SiO$_2$ Containing 1.35% Na$_2$O | | | | | | | | | | | | |
| Reaction Temp. (°C.) | 570 | 642 | 695 | 694 | 690 | 684 | 682 | 723 | 624 | 673 | 715 | 733 | 789 |
| Space Velocity | 1696 | 1696 | 1696 | 1696 | 1696 | 1696 | 1696 | 1696 | 1696 | 1696 | 1696 | 1696 | 1696 |
| CH$_4$/O$_2$ (mole ratio) | 30.0 | 30.0 | 30.0 | 30.0 | 30.0 | 30.0 | 30.0 | 30.0 | 29.9 | 29.9 | 29.9 | 29.9 | 29.9 |
| O$_2$ conversion (mole %) | 3.0 | 58.9 | 92.8 | 87.8 | 82.5 | 75.8 | 70.6 | 99.5 | 8.6 | 99.1 | 99.1 | 98.8 | 99.4 |
| CH$_4$ conversion (mole %) | .04 | 1.5 | 4.0 | 3.9 | 3.7 | 3.2 | 2.9 | 5.3 | 0.2 | 3.7 | 4.6 | 4.7 | 9.5 |
| Product Selectivity | | | | | | | | | | | | | |
| H$_2$ | — | — | — | — | — | — | — | — | — | — | — | — | — |
| CO | — | — | — | — | — | — | — | — | Present | — | — | — | — |
| CO$_2$ | 100 | 59.3 | 24.8 | 22.0 | 21.8 | 23.4 | 23.9 | 17.7 | 56.4 | 26.3 | 29.9 | 23.5 | 32.5 |
| C$_2$H$_4$ | (1) | 7.5 | 25.0 | 24.6 | 25.0 | 23.3 | 22.3 | 35.9 | 7.2 | 28.4 | 36.4 | 34.6 | 27.3 |
| C$_2$H$_6$ | (1) | 32.9 | 46.8 | 46.5 | 47.2 | 50.4 | 51.1 | 40.9 | 36.4 | 38.8 | 27.3 | 23.8 | 8.4 |
| C$_2$H$_2$ | (1) | — | — | — | — | — | — | — | — | 1.2 | — | — | — |
| C$_3$H$_8$ & C$_3$H$_6$ | (1) | 0.3 | 1.8 | 2.2 | 1.9 | 1.8 | 1.6 | 2.6 | — | 2.9 | 2.8 | 2.7 | 2.3 |
| i-C$_4$ | (1) | — | 0.6 | 1.3 | 2.6 | — | — | — | — | — | — | — | 0.2 |
| n-C$_4$ | (1) | — | 1.0 | 2.5 | 1.2 | 0.8 | 0.7 | 2.6 | — | — | — | — | — |
| 1-C$_4$ = | (1) | — | — | 0.9 | 0.4 | 0.3 | 0.3 | 0.3 | — | 0.2 | 0.3 | 0.3 | — |

TABLE 14-continued

| | Example | | | | | | | | | | | | |
|---|---|---|---|---|---|---|---|---|---|---|---|---|
| | 95 | 96 | 97 | 98 | 99 | 100 | 101 | 102 | 103 | 104 | 105 | 106 | 107 |
| Unidentified $C_4$ | (1) | — | — | — | — | — | — | — | — | — | 3.3 | 3.3 | 2.6 |
| Unidentified $C_6$ | (1) | — | — | — | — | — | — | — | — | — | — | 11.9[2] | 26.7[3] |
| Selectivity to $C_2+$ | (1) | 40.7 | 75.2 | 78.0 | 78.3 | 76.6 | 76.0 | 82.3 | 43.6 | 73.6 | 70.1 | 76.6 | 67.5 |
| Yield of $C_2+$ | (1) | 0.61 | 3.01 | 3.04 | 2.90 | 2.45 | 2.20 | 4.36 | 0.09 | 2.72 | 3.22 | 3.60 | 6.41 |
| $C_2H_4/C_2H_6$ (mole ratio) | (1) | 0.229 | 0.534 | 0.530 | 0.530 | 0.462 | 0.437 | 0.879 | 0.200 | 0.731 | 1.332 | 1.453 | 3.288 |

(1) Conversion was too low for accurate measurements.
(2) Benzene and Toluene
(3) Approximately 65% benzene

TABLE 15

| | Example | | | | | | | | | | |
|---|---|---|---|---|---|---|---|---|---|---|---|
| | 108 | 109 | 110 | 111 | 112 | 113 | 114 | 115 | 116 | 117 | 118 |
| Tube Packing | 20% PbO—Norton $SiO_2$ Containing 1.66% MgO | | | | | | | | | | |
| Reaction Temp. (°C.) | 658 | 706 | 757 | 807 | 853 | 876 | 876 | 785 | 691 | 810 | 863 |
| Space Velocity | 1696 | 1696 | 1696 | 1696 | 1696 | 1696 | 1696 | 3390 | 3390 | 3390 | 3390 |
| $CH_4/O_2$ (mole ratio) | 31.3 | 31.3 | 31.3 | 31.3 | 31.3 | 31.3 | 31.3 | 24.2 | 24.2 | 24.2 | 24.2 |
| $O_2$ conversion (mole %) | 48.9 | 77.3 | 99.5 | 99.5 | 99.5 | 99.5 | 99.5 | 99.5 | 33.2 | 99.6 | 99.5 |
| $CH_4$ conversion (mole %) | 0.8 | 1.8 | 2.2 | 2.6 | 3.0 | 3.0 | 3.3 | 3.2 | 1.0 | 3.4 | 3.6 |
| Product Selectivity | | | | | | | | | | | |
| $H_2$ | 26.2 | 3.2 | 3.0 | 13.9 | 47.2 | 70.8 | 63.4 | 4.2 | 15.0 | 2.1 | 12.9 |
| CO | — | 21.8 | 38.6 | 34.5 | 35.4 | 38.2 | 37.7 | 31.7 | 8.6 | 32.6 | 42.9 |
| $CO_2$ | 80.0 | 54.9 | 40.5 | 34.3 | 25.3 | 20.0 | 22.7 | 49.0 | 59.0 | 36.6 | 21.4 |
| $C_2H_4$ | 4.4 | 8.4 | 6.0 | 11.9 | 16.7 | 20.1 | 21.2 | 5.2 | 7.2 | 10.4 | 10.6 |
| $C_2H_6$ | 15.6 | 14.9 | 12.7 | 16.2 | 16.3 | 17.2 | 14.2 | 11.4 | 15.7 | 17.3 | 19.1 |
| $C_3H_8$ & $C_3H_6$ | — | — | 1.1 | 1.2 | 1.6 | 2.2 | 1.7 | 1.0 | 5.0 | 1.1 | 0.6 |
| i-$C_4$ | — | — | — | — | — | — | 0.4 | 0.2 | — | — | — |
| n-$C_4$ | — | — | — | 0.2 | 2.9 | 0.2 | — | 0.2 | — | 0.1 | — |
| i-$C_4$ = | — | — | — | — | — | 0.2 | 0.3 | — | — | — | 5.1 |
| Selectivity to $C_2+$ | 20.0 | 23.3 | 21.0 | 31.2 | 39.3 | 41.8 | 39.8 | 19.3 | 32.3 | 30.7 | 35.7 |
| Yield of $C_2+$ | 0.32 | 0.42 | 0.46 | 0.81 | 1.18 | 1.25 | 1.31 | 0.62 | 0.32 | 1.04 | 1.28 |
| $C_2H_4/C_2H_6$ (mole ratio) | 0.283 | 0.565 | 0.471 | 0.734 | 1.028 | 1.319 | 1.495 | 0.465 | 0.467 | 0.601 | 0.555 |

Additional experiments have shown that the incorporation of lithium, potassium or cesium also affords improved selectivities of the catalysts in the oxidative coupling reaction. By contrast, incorporation of an alkaline earth metal component into the catalyst was not beneficial. Higher $C_2H_4:C_2H_6$ mole ratios are desirable in order to increase the yield of aromatics formed by the oligomerization of ethylene in a subsequent step, as described hereinbelow in connection with Examples 169–187.

The level of metal component on the support was found to be important within broad ranges. As can be seen from Examples 119–127, all levels of lead oxide on Calsicat D silica were effective when compared with Calsicat D silica without lead oxide (Examples 5–10). However, the low levels of lead oxide, particularly 5.9%, tend to form some carbon monoxide at 800° C. as did the base silica itself, while the higher levels of lead oxide made less or none at all.

One problem with the use of lead oxide on silica is its tendency to deactivate. As illustrated in Table 10, the support must be calcined before impregnating with the reducible metal component to obtain a selective catalyst. However, it is also necessary to calcine the catalyst containing the reducible metal component at high temperature in the presence of oxygen to maintain a highly stable catalyst. Example 128–136 illustrate the influence of calcination after impregnation on catalyst performance. Without air calcination (Examples 128–130), activity and selectivity were high, but prolonged use of the catalyst above 800° C. caused the catalyst to deactivate. When calcined in air at 1000° C. for 16 hours (Examples 131–133), the catalyst showed surprisingly good activity and selectivity and could be used for prolonged periods with little loss of activity. Calcination in air at 1000° C. for sixty hours (Examples 134–136) likewise provided a highly selective and stable catalyst, although

TABLE 16

| | Example | | | | | | | | |
|---|---|---|---|---|---|---|---|---|---|
| | 119 | 120 | 121 | 122 | 123 | 124 | 125 | 126 | 127 |
| Tube Packing | Lead Oxide on Calsicat D Silica | | | | | | | | |
| PbO level (wt %) | 5.9% | | | 11.1% | | | 33.3% | | |
| Reaction Temp. (°C.) | 747 | 802 | 839 | 757 | 801 | 837 | 757 | 801 | 837 |
| Space Velocity | 1695 | 1695 | 1695 | 1695 | 1695 | 1695 | 1695 | 1695 | 1695 |
| $CH_4/O_2$ (mole ratio) | 23.5/1 | 23.5/1 | 23.5/1 | 23.7/1 | 23.7/1 | 23.7/1 | 24.0/1 | 24.0/1 | 24.0/1 |
| $O_2$ Conversion (mole %) | 72.2 | 99.1 | 99.3 | 60.8 | 69.0 | 99.1 | 47.7 | 67.3 | 99.0 |
| $CH_4$ Conversion (mole %) | 3.8 | 7.3 | 8.0 | 2.8 | 4.4 | 7.6 | 3.7 | 5.4 | 7.2 |
| Product Selectivity | | | | | | | | | |
| CO | — | 2.8 | 1.2 | — | 0.9 | 1.7 | — | — | — |

TABLE 16-continued

| | Example | | | | | | | | |
|---|---|---|---|---|---|---|---|---|---|
| | 119 | 120 | 121 | 122 | 123 | 124 | 125 | 126 | 127 |
| Tube Packing | Lead Oxide on Calsicat D Silica | | | | | | | | |
| PbO level (wt %) | | 5.9% | | | 11.1% | | | 33.3% | |
| $CO_2$ | 29.1 | 13.4 | 10.6 | 38.4 | 21.9 | 12.6 | 13.6 | 10.2 | 10.1 |
| $C_2H_4$ | 14.9 | 29.9 | 38.6 | 7.7 | 16.6 | 31.1 | 18.5 | 29.2 | 37.1 |
| $C_2H_6$ | 54.2 | 50.4 | 44.4 | 50.9 | 58.8 | 51.1 | 65.7 | 57.1 | 46.9 |
| $C_2H_2$ | — | 0.9 | 1.4 | — | 0.1 | 0.9 | 0.2 | 0.4 | 0.7 |
| $C_3$'s | 1.8 | 2.6 | 3.4 | 3.0 | 1.7 | 2.6 | 2.1 | 2.9 | 3.6 |
| $C_4$'s and higher | | 0.1 | 0.3 | — | — | — | — | 0.2 | — |
| Selectivity to $C_2^+$ | 70.9 | 83.9 | 88.1 | 61.6 | 77.2 | 85.7 | 86.5 | 89.8 | 88.3 |
| Yield of $C_2^+$ | 2.7 | 6.1 | 7.0 | 1.7 | 3.4 | 6.5 | 3.2 | 4.8 | 6.4 |

TABLE 17

| | Example | | | | | | | | |
|---|---|---|---|---|---|---|---|---|---|
| | 128 | 129 | 130 | 131 | 132 | 133 | 134 | 135 | 136 |
| Calcination Temp. (°C.) | 600 | 600 | 600 | 1000 | 1000 | 1000 | 1000 | 1000 | 1000 |
| Calcination Time (hr) | 16 | 16 | 16 | 16 | 16 | 16 | 60 | 60 | 60 |
| Air | no | no | no | yes | yes | yes | yes | yes | yes |
| Reaction Temp. (°C.) | 721 | 807 | 822 | 745 | 831 | 856 | 723 | 825 | 863 |
| Space Velocity | 1700 | 1700 | 1700 | 1700 | 1700 | 1700 | 1700 | 1700 | 1700 |
| $CH_4/O_2$ (mole rate) | 18.5/1 | 18.5/1 | 18.5/1 | 23.4/1 | 23.4/1 | 23.4/1 | 24.2/1 | 24.2/1 | 24.3/1 |
| $O_2$ Conversion (mole %) | 71.1 | 95.2 | 95.0 | 68.7 | 99.5 | 99.5 | 9.7 | 68.5 | 99.1 |
| $CH_4$ Conversion (mole %) | | | | 4.5 | 9.0 | 8.2 | 0.7 | 5.5 | 7.4 |
| Product Selectivity | | | | | | | | | |
| CO | — | — | 1.8 | — | 1.5 | — | — | 2.5 | 3.8 |
| $CO_2$ | 21.1 | 14.0 | 12.7 | 20.9 | 9.7 | 10.2 | 15.2 | 9.5 | 8.5 |
| $C_2H_4$ | 14.8 | 36.3 | 42.2 | 17.8 | 34.1 | 43.2 | 5.4 | 31.8 | 42.1 |
| $C_2H_6$ | 39.4 | 44.7 | 30.9 | 59.6 | 41.7 | 39.9 | 72.0 | 52.0 | 39.9 |
| $C_2H_2$ | — | — | 0.7 | — | 0.4 | — | — | 1.3 | 1.7 |
| $C_3$'s | 4.1 | 3.2 | 4.7 | 1.6 | 2.9 | 3.8 | 7.5 | 2.9 | 3.7 |
| $C_4$'s and higher | 20.7 | 1.7 | 7.1 | — | 11.4 | 1.0 | — | — | 0.4 |
| Selectivity to $C_2^+$ | 79.0 | 85.9 | 85.6 | 79.0 | 90.5 | 87.9 | 84.9 | 88.0 | 87.8 |
| Yield of $C_2^+$ | | | | 3.6 | 8.1 | 7.2 | 5.9 | 4.8 | 6.5 | some of its original activity was lost, particularly at low coupling temperatures. It is believed that lead oxide in calcination reacts with the silica base to form some form of lead silicate. In the presence of air this compound presumably is maintained in its highest valence state.

The conditions employed to calcine the oxidative coupling catalysts employed in Examples 5-27 and 32-187 are summarized in Table 18.

Other lead compounds have been shown to give good selectivities for the formation of coupled products, depending on the nature of the anion. Lead sulfate (Example 137-141) was relatively unattractive until it was exposed to prolonged reaction conditions. During this period, $SO_2$ was evolved making a new and more selective species. Lead sulfide (Examples 142-144) was active from the beginning and afforded high selectivity for the formation of coupled products but tended to deactivate with time. Lead tungstate (Examples 145-147) was moderately selective at low temperatures. Lead molybdate (Examples 148-149) was much less selective even at low temperatures. In each of Examples 137-149, the lead compound was supported on a Calsicat D support. Preferred anions are those that can decompose to form a lead oxide type of compound.

Catalysts containing compounds of reducible metals other than lead are less selective when tested in the oxidative coupling reaction under similar conditions. For example, vanadia on Calsicat D silica afforded only a 22% selectivity for the formation of coupled products. Manganese oxide on Calsicat D silica afforded 50-64% selectivity for the formation of coupled products. Indium oxide on Calsicat D silica afforded a 31-45% selectivity for the formation of coupled products.

EXAMPLES 150-155

All of the examples of the oxidative coupling reaction presented in Examples 1-149 were performed using a

TABLE 18

| Example | Conditions of Calcination Before Impregnation | Surface Area ($m^2$/gm) Before Impregnation | Conditions of Calcination After Impregnation |
|---|---|---|---|
| 5-10[1] | 8 hrs at 1000° C. | 24 | |
| 11-13[1] | used as received | <5 | |
| 14-17 | used as received | 24 | |
| 18-21[1] | 2 hrs at 600° C. | <5 | |
| 22-25[1] | 2 hrs at 600° C. | 44 | |
| 26[1] | 2 hrs at 600° C. | — | |
| 27[1] | 2 hrs at 600° C. | — | |
| 32-35[1] | 2 hrs at 743° C. | — | |
| 36-38 | — | 4 | 2 hrs at 600° C. |
| 39-46 | used as received | 24 | 2 hrs at 600° C. |
| 47-49 | used as received | 245 | 2 hrs at 600° C. |
| 50 | 2 hrs at 650° C. | 239 | 2 hrs at 600° C. |
| 51 | 8 hrs at 830° C. | 179 | 2 hrs at 600° C. |
| 52 | 8 hrs at 920° C. | 116 | 2 hrs at 600° C. |
| 53 | 8 hrs at 970° C. | 21 | 2 hrs at 600° C. |
| 54 | 4 hrs at 1000° C. | <2 | 2 hrs at 600° C. |
| 55-59 | 8 hrs at 920° C. | 116 | 2 hrs at 600° C. |
| 60-118 | 2-3 hrs at 550-660° C. | — | 2 hrs at 600° C. |
| 119-127 | used as received | 24 | 2 hrs at 600° C. |
| 128-130 | used as received | 24 | 16 hrs at 600° C. |
| 131-133 | used as received | 5[2] | 16 hrs at 1000° C. |

TABLE 18-continued

| Example | Conditions of Calcination Before Impregnation | Surface Area (m²/gm) Before Impregnation | Conditions of Calcination After Impregnation |
|---|---|---|---|
| 134–136 | used as received | 4[2] | 60 hrs at 1000° C. |
| 137–168 | used as received | 24 | 2 hrs at 600° C. |

[1]Not impregnated
[2]Surface area after impregnation

TABLE 19

| | Example | | | | | | | | | | | | |
|---|---|---|---|---|---|---|---|---|---|---|---|---|
| | 137 | 138 | 139 | 140 | 141 | 142 | 143 | 144 | 145 | 146 | 147 | 148 | 149 |
| | Tube Packing 20% PbSO₄ | | | | | Lead Compound 20% PbS | | | | Tube Packing 20% PbWO₄ | | 20% PbMoO₄ | |
| Reaction Temp. (°C.) | 715 | 756 | 803 | 842 | 830 | 757 | 805 | 858 | 742 | 807 | 879 | 763 | 863 |
| Space Velocity | 1695 | 1695 | 1695 | 1695 | 3390 | 1690 | 1690 | 1690 | 3390 | 3390 | 3390 | 1695 | 1695 |
| CH₄/O₂ (mole ratio) | 22.7/1 | 22.7/1 | 22.7/1 | 22.8/1 | 22.1/1 | 23.0/1 | 23.1/1 | 23.1/1 | 22.3/1 | 22.3/1 | 22.3/1 | 23.8/1 | 23.8/1 |
| O₂ Conversion (mole %) | 99.4 | 99.3 | 99.4 | 99.2 | 99.4 | 82.7 | 99.0 | 99.4 | 62.4 | 99.3 | 99.1 | 99.4 | 99.0 |
| CH₄ Conversion (mole %) | 8.5 | 7.3 | 6.9 | 7.3 | 8.3 | 6.4 | 7.3 | 8.7 | 3.2 | 5.4 | 7.3 | 3.6 | 4.7 |
| Product Selectivity | | | | | | | | | | | | | |
| CO | — | — | 0.3 | 1.7 | 3.4 | — | — | — | — | 7.4 | 44.5 | 6.7 | 43.9 |
| CO₂ | 58.5 | 31.9 | 19.9 | 17.0 | 12.2 | 20.5 | 13.1 | 10.3 | 36.5 | 36.1 | 26.7 | 65.5 | 40.3 |
| C₂H₄ | 7.3 | 16.7 | 30.5 | 42.7 | 32.9 | 19.4 | 32.6 | 42.2 | 8.1 | 12.3 | 5.4 | 2.6 | 2.7 |
| C₂H₆ | 28.6 | 36.7 | 45.5 | 32.8 | 47.6 | 55.6 | 51.2 | 34.6 | 51.1 | 42.4 | 21.4 | 24.6 | 10.8 |
| C₂H₂ | — | — | 0.6 | 0.5 | 0.7 | 0.1 | 0.4 | 2.3 | 1.5 | — | 0.9 | — | 1.6 |
| C₃'s | 1.0 | 2.4 | 2.3 | 4.0 | 2.9 | 1.8 | 2.8 | 4.3 | 2.2 | 1.8 | 1.0 | 0.6 | 0.7 |
| C₄'s | 4.6 | 12.3 | 0.9 | 1.3 | 0.2 | 1.2 | — | 6.4 | 0.7 | — | — | — | — |
| Selectivity to C₂⁺ | 41.5 | 68.1 | 79.8 | 81.3 | 84.3 | 78.1 | 87.0 | 89.8 | 63.6 | 56.5 | 28.7 | 27.8 | 15.8 |
| Yield of C₂⁺ | 3.5 | 5.0 | 5.0 | 5.9 | 7.0 | 5.0 | 6.4 | 7.8 | 1.9 | 3.1 | 2.1 | 1.0 | 0.7 | this undesirable effect illustrated in Examples 154–155. Examples 156–168 were performed using the same general

TABLE 20

| | Example | | | | | |
|---|---|---|---|---|---|---|
| | 150 | 151 | 152 | 153 | 154 | 155 |
| Reaction Temp. (°C.) | 829 | 896 | 915 | 914 | 836 | 836 |
| Space Velocity | 6600 | 3300 | 1320 | 1320 | 1690 | 1690 |
| Recycle | No | | | | Yes | | once-through operational mode, with no attempt being made to recover and recycle the unreacted feedstock alkane. In order to increase the conversion of the feedstock alkane and the yield of desired products therefrom, it is desirable to recycle unused feedstock alkane. However, the use of simple recycle of the entire product mixture formed in the oxidative coupling reaction is not particularly advantageous as shown in Examples 150–155. Examples 150–155 were performed using the same general procedure as used in Examples 39–46, except that in Examples 154–155 the product was recycled. The catalyst employed in Examples 150–155 was a Calsicat D silica support (that had not been calcined prior to impregnation) containing 20% by weight of PbO that was calcined for 2 hours at 600° C. after impregnation.

Examples 150–153 show the performance of a lead oxide catalyst on Calsicat D silica in a once-through mode. As is seen, even at the lowest CH₄/O₂ mole ratio of 5.2/1 (Example 153), the selectivity for the formation of coupled products was respectable, but the conversion of methane and yield of coupled products were at best only about 19% and 14%, respectively.

Surprisingly, however, when the entire gaseous product mixture from the oxidative coupling reaction was recycled to the oxidative coupling step (Examples 154–155), selectivity for the formation of coupled products dropped drastically into the range of 42–61%, even with high mole ratios of CH₄/O₂ in the total incoming gas, and the yield of desired product (obtained as the product of the CH₄ conversion multiplied by the selectivity for the formation of coupled products, divided by 100) was no better than with once-through operations.

EXAMPLES 156–168

Examples 156–168 involve a systematic study to find the components in recycle gas that are responsible for

| | | | | | | |
|---|---|---|---|---|---|---|
| CH₄/O₂ (mole ratio) in makeup feed | 18.7/1 | 19.9/1 | 10.3/1 | 5.2/1 | 8.4/1 | 8.4/1 |
| CH₄/O₂ (mole ratio) in total feed | 18.7/1 | 19.9/1 | 10.3/1 | 5.2/1 | 33.2/1 | 24.5/1 |
| O₂ Conversion (mole %) | 33.7 | 92.3 | 100.0 | 88.7 | 96.4 | 94.9 |
| CH₄ Conversion (mole %) | 3.4 | 8.5 | 13.4 | 18.7 | 9.5 | 22.0 |
| Product Selectivity | | | | | | |
| CO | 0.0 | 0.0 | 0.0 | 6.6 | 6.5 | 6.7 |
| CO₂ | 8.3 | 9.6 | 14.2 | 18.3 | 32.9 | 51.1 |
| C₂H₄ | 19.7 | 37.4 | 43.6 | 30.2 | 32.7 | 25.3 |
| C₂H₆ | 70.4 | 42.4 | 26.2 | 20.2 | 14.0 | 9.8 |
| C₂H₂ | 0.0 | 2.8 | 2.0 | 0.0 | 0.7 | 0.6 |
| C₃'s | 1.7 | 7.5 | 7.2 | 19.5 | 4.7 | 3.2 |
| C₄'s | 0.0 | 0.4 | 6.8 | 5.6 | 8.0 | 2.7 |
| Selectivity to C₂⁺ | 91.8 | 90.5 | 85.8 | 75.5 | 60.1 | 41.6 |
| Yield of C₂⁺ | 3.1 | 7.7 | 11.5 | 14.1 | 5.7 | 9.2 | procedure as used in Examples 39–46, except as indicated herein. The catalyst employed in Examples 156–168 was a Calsicat D silica support (that had not been calcined prior to impregnation) containing 20% by weight of PbO that was calcined for 2 hours at 600° C. after impregnation. By spiking methane feed to the oxidative coupling reaction with nitrogen, carbon monoxide, carbon dioxide and water, it was observed that none of these materials had a deleterious effect. Residual olefins and acetylene in the recycle gas, however, did have an undesirable effect in the oxidative coupling reaction. Ethane itself did not. The effect of ethane in the oxidative coupling reaction is shown in Examples 156–161. A blend of 10% ethane and 90% methane showed a surprising increase of both selectivity and yield for ethylene and higher products. Even a 100% ethane feedstock was converted to unsaturates in high selectivity and yield. Accountability of carbons across the system was essentially 100%, indicating little tendency to form coke. On the other hand, the presence of ethylene in the feedstock to the oxidative coupling reactor had a deleterious effect, even at levels of 1% in methane, as shown in Examples 162-168. Of particular concern was the observation that accountability of carbons across the system was poor, as a result of coke formation. Thus, in order to increase the degree of conversion of the feedstock alkane and the yield of the desired products therefrom, the recycle gas must be substantially free of ethylene and other higher unsaturates to preserve the high selectivity of an oxidative coupling catalyst for methane coupling, but it is advantageous that ethane is present in the feed or recycle.

TABLE 21

| | Examples | | | | | |
|---|---|---|---|---|---|---|
| | 156 | 157 | 158 | 159 | 160 | 161 |
| Feed | 10% $C_2H_6$ in $CH_4$ | | | 100% $C_2H_6$ | | |
| Reaction Temp. (°C.) | 783 | 838 | 847 | 739 | 787 | 823 |
| Space Velocity | 6600 | 6600 | 3300 | 6600 | 6600 | 6600 |
| $CH_4/O_2$ (mole ratio) | 16.8/1 | 16.8/1 | 17.6/1 | — | — | — |
| $C_2H_6/O_2$ (mole ratio) | 1.76/1 | 1.76/1 | 1.89/1 | 11.5 | 11.5 | 5.4 |
| $O_2$ Conversion (mole %) | 30.0 | 85.3 | 100 | 59.2 | 100 | 100 |
| $C_2H_6$ Conversion (mole %) | 19.2 | 44.2 | 66.5 | 9.7 | 27.3 | 62.5 |
| Product Selectivity | | | | | | |
| CO | — | — | — | 0.15 | 2.1 | 3.9 |
| $CO_2$ | 6.9 | 5.4 | 3.3 | 1.3 | 0.6 | 0.8 |
| $CH_4$ | — | — | — | 2.4 | 2.9 | 5.2 |
| $C_2H_4$ | 89.6 | 89.2 | 86.2 | 92.0 | 88.2 | 84.0 |
| $C_2H_6$ | — | — | — | — | — | — |
| $C_2H_2$ | — | 0.8 | 2.3 | — | 2.5 | 3.0 |
| $C_3$'s | 3.5 | 4.7 | 6.3 | 4.1 | 1.8 | 2.2 |
| $C_4$'s | | | 2.0 | — | 2.0 | 0.8 |
| Selectivity to $C_2+$ | 93.1 | 94.7 | 96.8 | 96.1 | 94.5 | 90.0 |
| Yield of $C_2+$ | 17.9 | 41.9 | 64.3 | 9.3 | 25.8 | 56.3 |

TABLE 22

| | Example | | | | | | |
|---|---|---|---|---|---|---|---|
| | 162 | 163 | 164 | 165 | 166 | 167 | 168 |
| Feed, % $C_2H_4$ in $CH_4$ | 0 | 0.8 | 1.4 | 10 | 10 | 100 | 100 |
| Temp. (°C.) | 815 | 814 | 811 | 746 | 795 | 733 | 836 |
| Space Velocity | 6600 | 6600 | 6600 | 6600 | 6600 | 6600 | 3300 |
| $CH_4/O_2$ (mole ratio) | 24.1/1 | 25.9/1 | 27.3/1 | 18.0/1 | 18.0/1 | — | — |
| $C_2H_4/O_2$ (mole ratio) | — | — | — | 2.3/1 | 2.3/1 | 16.8/1 | 2.3/1 |
| $O_2$ Conversion (mole %) | 52.6 | 64.4 | 67.3 | 85.0 | 99.7 | 71.8 | 100 |
| $C_2H_4$ Conv. (mole %) | — | — | — | 14.7 | 20.6 | 4.2 | 62.6 |
| Product Selectivity | | | | | | | |
| CO | — | — | — | 1.4 | 0.1 | 44.1 | 29.0 |
| $CO_2$ | 8.5 | 15.6 | 18.1 | 25.1 | 21.9 | ? | 16.1 |
| $CH_4$ | — | — | — | — | — | 9.0 | 16.1 |
| $C_2H_4$ | 28.0 | 15.1 | 2.4 | — | — | — | — |
| $C_2H_6$ | 47.8 | 47.9 | 61.1 | 26.0 | 27.8 | 7.9 | 4.8 |
| $C_2H_2$ | — | — | 4.3 | 4.7 | 6.2 | 5.9 | 1.9 |
| $C_3$'s | 15.8 | 17.3 | 8.9 | 9.9 | 13.8 | 26.1 | 5.6 |
| $C_4$'s+ | — | — | 5.2 | 32.9 | 30.3 | 7.0 | 20.9 |
| Selectivity to $C_2+$ | 91.6 | 80.3 | 81.9 | 73.5 | 78.1 | 46.9 | 33.2 |

EXAMPLE 169

The oxidative dehydrogenation step of the method of this invention is exemplified by Examples 169-171. In Example 169, a mixture of 10% ethane and 90% methane was blended with air to give a 1.89/1 ethane/oxygen ratio and passed over a 20% lead oxide catalyst on Calsicat D at 847° C. and space velocity of 3300. The exit gas showed a 66.5% conversion of ethane to ethylene with an 88% selectivity for ethylene.

EXAMPLE 170

100% ethane was passed through the same catalyst as employed in Example 169 at 823° C. and a space velocity of 6600, using an ethane to oxygen ratio of 5.4. Under these conditions 62.5% of the ethane was converted to ethylene with an 84% selectivity to ethylene.

EXAMPLE 171

The procedure of Example 170 was repeated with a low surface silica alone (Calsicat D) and found to give essentially the same results.

EXAMPLE 172

The use of the first charcoal bed is exemplified by Examples 172-174. In Example 172, a gaseous mixture containing 69% $N_2$, 3% methane, 3% $CO^2$, 10% ethane and 15% ethylene was passed through 450 grams of coconut charcoal at a flow rate of 607 cc/minute at room temperature. By gas chromatographic analysis it was observed that pure nitrogen exited the bed for 25 minutes at which point methane began to appear in the exit gas. At 65 minutes $CO_2$ began to appear, at 85 minutes ethylene began to exit the bed, and at 95 minutes ethane appeared at the exit. At this point the weight of $C_2+$ held by the charcoal was 0.037 gm/gm. The bed was then subjected to superheated steam and in less than 5 minutes essentially all adsorbed hydrocarbons were removed. The bed, after cooling and drying with nitrogen, was returned to service with essentially the same time for adsorption and desorption.

EXAMPLE 173

The procedure of Example 172 was repeated, except that when the bed became saturated the charcoal was evacuated at 29.0 inches of mercury vacuum at ambient temperature. Within twenty minutes essentially all the $C_2$ products were desorbed and the charcoal bed, when returned to service, possessed its original capacity for adsorption of the components of the gaseous mixture.

EXAMPLE 174

The procedure of Example 172 was repeated except that when the bed became saturated, the charcoal was heated to above 80° C. with superheated steam and then evacuated to 20 inches of mercury vacuum. The adsorbed components were essentially removed by the time the evacuation had attained 20 inches of mercury vacuum. The bed subsequently was found to be effective when returned to service.

EXAMPLE 175

Since air is preferably added to the system in the oxidative coupling and oxidative dehydrogenation steps, a slip stream of the recycle gas is vented to prevent a buildup of nitrogen and, unless removed in the first charcoal bed, carbon dioxide in the gas that is recycled to the oxidative coupling step. The slip stream which is vented contains about 10–20% of the unreacted methane. We have found that, by passing the slip stream through a second bed of coconut charcoal, not only is the methane recovered, but also both nitrogen and, unless removed in the first charcoal bed, carbon dioxide in the slip stream are vented and prevented from building up in the recycle gas. As a mixture comprising nitrogen, carbon dioxide and methane was passed through a bed of coconut charcoal, a stream of nitrogen largely devoid of hydrocarbons passed out of the bed. As the adsorption was continued, the other components of the stream passed out of the bed in this order: methane and carbon dioxide. When the bed became saturated with methane, methane began to pass out of the bed, and the charcoal bed was removed from service and replaced in service by a fresh charcoal bed. The components adsorbed on the saturated bed were desorbed with vacuum, in the order: methane and then carbon dioxide. Hence, by judicious use of vacuum, fractions rich in methane and carbon dioxide were isolated. The desorbed methane is returned back to the system, and nitrogen and carbon dioxide rejected, thus permitting a nearly complete return of methane to the system with high ultimate conversion and a minimal buildup of nitrogen and carbon dioxide in the system. With about a 20-minute adsorption of components from the slip stream and a 10-minute desorption of the adsorbed methane, a charcoal bed was able to be placed on a fast cycle for economic separation of components.

From the above description, it is apparent that the objects of the present invention have been achieved. While only certain embodiments have been set forth, alternative embodiments and various modifications will be apparent from the above description to those skilled in the art. These and other alternatives are considered equivalents and within the spirit and scope of the present invention.

Having described the invention, what is claimed is:

1. A method for converting at least one feedstock alkane containing from 1 to 3 carbon atoms to more valuable, heavier hydrocarbons, comprising:
   (a) contacting the feedstock alkane containing from 1 to 3 carbon atoms with an oxygen-containing gas in a reactor in the presence of an oxidative coupling catalyst at a temperature in the range of from about 600° C. to about 1,000° C., to thereby produce a gaseous mixture comprising any remaining unreacted feedstock alkane and oxygen and saturated and unsaturated aliphatic hydrocarbon products having higher molecular weights than the feedstock alkane from which they were formed, wherein the oxidative coupling catalyst comprises silica free of a reducible metal compound and having a surface area of from about 5 $m^2$/gm to about 175 $m^2$/gm, and
   (b) contacting the resulting gaseous mixture with an oxidative dehydrogenation catalyst under oxidative dehydrogenation conditions in a reactor to thereby dehydrogenate the saturated aliphatic hydrocarbon product and produce a gaseous mixture comprising any remaining unreacted feedstock alkane and oxygen and unsaturated aliphatic hydrocarbon product.

2. The method of claim 1 comprising additionally:
   (d) recycling to step (a) at least a portion of at least the remaining unreacted feedstock alkane component of the gaseous mixture produced in step (b).

3. The method of claim 2 comprising additionally:
   (c) after step (b) and prior to step (d), separating the unsaturated aliphatic hydrocarbon product from the gaseous mixture produced in step (b).

4. The method of claim 3 wherein the oxygen-containing gas comprises air, the gaseous mixture produced in step (a) comprises additionally nitrogen and carbon dioxide and the gaseous mixture remaining after step (b) comprises nitrogen, carbon dioxide, any remaining unreacted feedstock alkane and oxygen and higher molecular weight unsaturated aliphatic hydrocarbon product.

5. The method of claim 4 comprising additionally separating at least a portion of the nitrogen and carbon dioxide components from at least a portion of the gaseous mixture from step (b) and then recycling the remaining unreacted feedstock alkanes in such portion of the gaseous mixture of step (a).

6. The method of claim 1 wherein the feedstock alkane comprises methane, wherein ethane and ethylene are produced in step (a), and wherein at least a portion of the ethane is converted to ethylene in step (b).

7. The method of claim 1 wherein step (a) is performed at a temperature in the range of from about 700° C. to about 850° C.

8. The method of claim 1 wherein step (a) is performed under a total pressure in the reactor in the range of from about 1 atm. to about 10 atm.

9. The method of claim 1 wherein the ratio of the combined feedstock alkane partial pressure-to-the oxygen partial pressure at the entrance to the reactor in step (a) is in the range of from about 2:1 to about 40:1.

10. The method of claim 1 wherein step (a) is performed at a space velocity of from about 100 to about 10,000 volumes of total feed gas per volume of catalyst per hour.

11. The method of claim 1 wherein the silica free of a reducible metal compound is calcined at a temperature of from about 800° C. to about 1100° C. for from about 2 hr. to about 36 hr.

12. The method of claim 1 wherein step (b) is performed at a temperature in the range of from about 500° C. to about 900° C.

13. The method of claim 1 wherein step (b) is performed at a total absolute pressure in the range of from about 1 atm. to about 5 atm.

14. The method of claim 1 wherein step (b) is performed at a space velocity in the range of from about 100 to about 10,000 volumes of gas per volume of catalyst per hour.

15. The method of claim 1 wherein the ratio of the partial pressure of the saturated aliphatic hydrocarbon product in the gaseous mixture produced in step (a)-to-the oxygen partial pressure at the entrance to the reactor in step (b) is in the range of from about 40 to about 2.

16. The method of claim 15 wherein an oxygen-containing gas is added to the gaseous mixture produced in step (a) to bring the oxygen partial pressure at the entrance to the reactor in step (b) to the aforesaid level.

17. The method of claim 1 wherein the oxidative dehydrogenation catalyst comprises an amorphous refactory inorganic oxide comprises an oxide of Group IIA, IIIA, IIIB, IVA, or IVB of the Periodic Table.

18. The method of claim 17 wherein the oxidative dehydrogenation catalyst comprises silica.

19. The method of claim 3 wherein the separation in step (c) is effected by contacting the gaseous mixture produced in step (b) with a first adsorbent under conditions such that essentially all of the unsaturated hydrocarbon products having higher molecular weights than the feedstock alkane are adsorbed thereon and the unreacted feedstock alkane is not adsorbed thereon.

20. The method of claim 4 wherein the separation in step (c) is effected by contacting the gaseous mixture produced in step (b) with a first adsorbent under conditions such that at least a substantial portion of the unsaturated hydrocarbon products having higher molecular weights than the feedstock alkane are adsorbed thereon and nitrogen and the unreacted feedstock alkane are not adsorbed thereon.

21. The method of claim 20 wherein adsorption of the hydrocarbon products is effected at a temperature of up to about 60° C. at substantially atmospheric pressure absolute.

22. The method of claim 21 wherein the adsorbed hydrocarbon products are desorbed in steam at a temperature of 100°–150° C.

23. The method of claim 21 wherein the adsorbed hydrocarbon products are desorbed by evacuation of the first adsorbent.

24. The method of claim 20 wherein the separation of nitrogen is effected by contacting the gaseous mixture remaining after step (c) with a second adsorbent under conditions such that at least a substantial portion of the unreacted feedstock alkane is adsorbed thereon and the nitrogen is not adsorbed thereon.

25. The method of claim 24 wherein the carbon dioxide is also adsorbed on the first adsorbent and thereby separated from the gaseous mixture.

26. The method of claim 24 wherein the carbon dioxide is also adsorbed on the second adsorbent and thereby separated from the gaseous mixture.

27. The method of claim 24 wherein desorption of the unreacted feedstock alkane is effected by evacuation of the second adsorbent.

* * * * *

UNITED STATES PATENT OFFICE
CERTIFICATE OF CORRECTION

Patent No. 4,751,336     Dated JUNE 14, 1988

Inventor(s): JAMES L. JEZL - GLENN O. MICHAELS - MICHAEL J. SPANGLER

It is certified that error appears in the above-identified patent and that said Letters Patent is hereby corrected as shown below:

| Col. | Line | |
|---|---|---|
| 1 | 21 | "keller" should be -- Keller -- |
| 2 | 40 | "preferfed" should be -- preferred -- |
| 3 | 41-42 | "catalytically; dehydrogenated" should be -- catalytically dehydrogenated -- |
| 3 | 42 | "ethylene (c)" should be -- ethylene; (c) -- |
| 4 | 65 | "pressures" should be -- pressure -- |
| 5 | 42 | "in" should be -- is -- |
| 5 | 43 | "vanadium" should be -- vanadium, -- |
| 5 | 64 | "aluminia" should be -- alumina -- |
| 6 | 44 | "oxidation" should be -- oxidative -- |
| 8 | 7 | "alunina" should be -- alumina -- |
| 8 | 17 | "dehydragenation" should be -- dehydrogenation -- |
| 9 | 68 | "absolute. To" should be -- absolute to -- |
| 14 | 37 | "are" should be -- area -- |
| 15 | 55 | "Example" should be -- Examples -- |
| 20 | 43 | "Example" should be -- Examples -- |
| 21 | 49 | "Example" should be -- Examples -- |
| 26 | 3 | "and space" should be -- and a space -- |

14   17 Table 8    "$C_4$'s" should be -- $C_4$'s+ --

14 Table 9    "Calsicat D Silica (245 $m^2$/g)" should be -- Calsicat D Silica (24 $m^2$/g) --

14 Table 9    "20/1   5.2/1   10/1   10/1   10.3/1" should be -- 20/1   10.3/1   5.2/1   10/1   10/1   10/1 --

UNITED STATES PATENT OFFICE
CERTIFICATE OF CORRECTION

Patent No. 4,751,336     Dated JUNE 14, 1988

Inventor(s) JAMES L. JEZL - GLENN O. MICHAELS - MICHAEL J. SPANGLER

It is certified that error appears in the above-identified patent and that said Letters Patent is hereby corrected as shown below:

| Col. | Line | | |
|---|---|---|---|
| 17 | Table 13 | "$C_2H_8$ & $C_3H_6$" should be | -- $C_3H_8$ & $C_3H_6$ -- |
| 28 | 34 | "of" should be | -- to -- |
| 29 | 11 | "refactory" should be | -- refractory -- |

Signed and Sealed this

Eleventh Day of July, 1989

*Attest:*

DONALD J. QUIGG

*Attesting Officer*     *Commissioner of Patents and Trademarks*